United States Patent
Roedel et al.

(10) Patent No.: US 9,540,702 B2
(45) Date of Patent: *Jan. 10, 2017

(54) STABILIZATION OF ENZYMES WITH STABLE COENZYMES

(75) Inventors: Wolfgang Roedel, Heidelberg (DE); Carina Horn, Biblis (DE); Nelli Steinke, Lampertheim (DE); Nadine Bucci, Wiesloch (DE); Thomas Meier, Munich (DE); Rainer Schmuck, Benediktbeuern (DE); Rolf Nagel, Buerstadt (DE); Dieter Heindl, Paehl (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 964 days.

This patent is subject to a terminal disclaimer.

(21) Appl. No.: 13/400,209

(22) Filed: Feb. 20, 2012

(65) Prior Publication Data

US 2012/0276565 A1 Nov. 1, 2012

Related U.S. Application Data

(63) Continuation of application No. PCT/EP2010/062045, filed on Aug. 18, 2010.

(30) Foreign Application Priority Data

Aug. 20, 2009 (EP) .................................... 09168327

(51) Int. Cl.
C12N 9/04 (2006.01)

(52) U.S. Cl.
CPC ..... *C12Y 101/01001* (2013.01); *C12N 9/0006* (2013.01); *C12Y 101/01002* (2013.01); *C12Y 101/01047* (2013.01); *C12Y 101/01049* (2013.01); *C12Y 106/05002* (2013.01)

(58) Field of Classification Search
None
See application file for complete search history.

(56) References Cited

U.S. PATENT DOCUMENTS

| | | |
|---|---|---|
| 5,032,506 A | 7/1991 | Palmer et al. |
| 5,801,066 A | 9/1998 | Meikle |
| 6,710,770 B2 * | 3/2004 | Tomasi et al. ................ 345/168 |
| 7,553,615 B2 | 6/2009 | Heindl et al. |
| 2007/0196899 A1* | 8/2007 | Goto et al. ................... 435/69.1 |

FOREIGN PATENT DOCUMENTS

| | | |
|---|---|---|
| EP | 2 093 284 A1 | 8/2009 |
| WO | WO 97/19190 | 5/1997 |

(Continued)

OTHER PUBLICATIONS

Scopes et al., Eur. J. Biochem. 251, 382-388 (1998).*

(Continued)

*Primary Examiner* — Alexander Kim

(57) ABSTRACT

Methods for stabilizing an enzyme by storing the enzyme in the presence of a stabilized coenzyme are disclosed. In addition, an enzyme stabilized with a stabilized coenzyme as well as the use thereof in test elements for detecting analytes are also disclosed. Other aspects include unique compositions, methods, techniques, systems and devices involving enzyme stabilization.

11 Claims, 28 Drawing Sheets

(56) References Cited

FOREIGN PATENT DOCUMENTS

| WO | WO 98/33936 | 8/1998 |
|----|----|----|
| WO | WO 01/49247 | 7/2001 |
| WO | WO 01/94370 | 12/2001 |
| WO | WO 2007/012494 A1 | 2/2007 |
| WO | WO 2008/075072 A2 | 6/2008 |

OTHER PUBLICATIONS

Ribas de Pouplana et al., Biochemical J. 276, 433-438 (1991).*
Slama et al., Biochemistry 28, 7688-7694.*
Slama et al., Carbanicotinamide Adenine Dinucleotide: Synthesis and Enzymological Properties of a Carboxcyclic Analogoue of Oxidized Nicotinamide Adenine Dinucleotide., Biochemistry (1988), vol. 27, pp. 183-193.*
UniProtKB-P27250 (last viewed on Jul. 21, 2015).*
Berrios-Rivera et al., Metabolic Engineering of *Escherichia coli*: Increase of Nadh Availability by Overexpressing an NAD+- dependent Formate Dehydrogenase., Metabolic Engineering (2002), vol. 4, pp. 217-229.*
An introduction to Humidity (last viewed on Jul. 21, 2015).*
UniProtKB-Q04894 (last viewed on Jul. 21, 2015).*
UniProtKB-P0AC54 (last viewed on Jul. 21, 2015).*
ExPASy ENZYME entry EC 1.6.5.2 (last viewed on Jul. 21, 2015).*
Barrio et al., A Fluorescent Analog of Nicotinamide Adenine Dinucleotide., Proc. Nat. Acad. Sci. (1972), vol. 69, pp. 2039-2042.*
W.A.Wood, Methods in Enzymology vol. XLI Carbohydrate Metabolism Part B, 1975, 7 pages, Academic Press, New York, San Francisco, London.
Munir et al.; Separation and Properties of Two Novel NADP+-dependent Alcohol Dehydrogenases from *Euglena gracilis* Z; Pakistan Journal of Biological Sciences, vol. 9, No. 15 (Dec. 31, 2006), p. 2743-2747.
Osborne et al.; An Investigation of the Nlcotinamide-Adenine Dinucleotide . . . ; Biochem J. (1976); 157, 255-259; XP 022553207.
Zhao et al.; Structural basis for nicotinamide cleavage and . . . ; PNAS, 2004 vol. 101, No. 23, 8563-8568; XP 0025532089.
International Search Report; PCT/EP2010/062045, Nov. 2010.
Tedeschi et al.; The Journal of Biological Chemistry, vol. 270, No. 6, 2512-2516 (1995) Need Copy.
Tedeschi et al.; The Journal of Biological Chemistry, vol. 270, No. 3, 1198-1204 (1995) Need Copy.

* cited by examiner

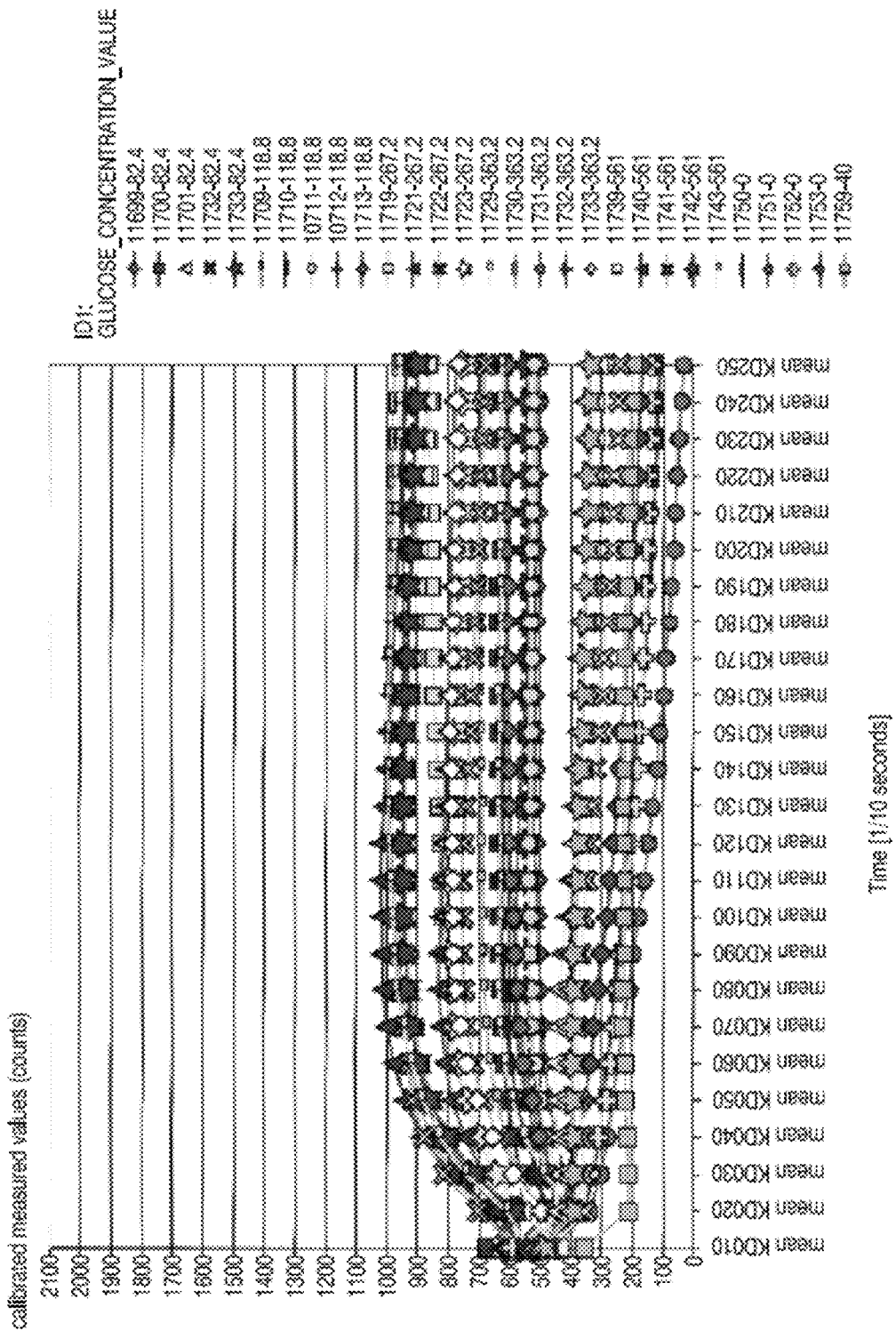

GlucDH_E96G_E170K

MYPDLKGKVVAITGAASGLGKAAMAIRFGKE
QAKVVINYYSNKQDPNEVKEEVIKEFGTLDIMI
VVQGDVTKEEDVKNIVQTAIKDWDKVIGTNLTGA
NNAGLGNPVPSHEMPLKDKNIKGNVINMSSVHEVI
FLGSREAIKYFVEENDIKGIKLMTKTLALEYAPKG
PWPLFVHYAASKGGAINTPINAEKFADPKQKADVE
IRVNNIGPGAINTPINAEKFADPKQKADVE
SMIPMGYIGEPEEIAVAVWLASKESSYVT
GITLFADGGMTKYPSFQARG

GlucDH_E170K_K252L

MYPDLKGKVVAITGAASGLGKAAMAIRFGKE
QAKVVINYYSNKQDPNEVKEEVIKEFGTLDIMI
VVQGDVTKEEDVKNIVQTAIKDWDKVIGTNLTGA
NNAGLGNPVPSHEMPLKDKNIKGIKLMTKTLALEYAPKG
PWPLFVHYAASKGGAINTPINAEVAVWLASKESSYVT
IRVNNIGPGAINTPINAEVAVWLASKESSYVT
SMIPMGYIGEPEEIAVAVWLASKESSYVT
GITLFADGGMTLYPSFQARG

*Fig. 21*

STABILIZATION OF ENZYMES WITH STABLE COENZYMES

CROSS-REFERENCE TO RELATED APPLICATIONS

This application is a continuation of International Application No. PCT/EP2010/062045 filed Aug. 18, 2010, which claims priority to European Patent Application No. 09168327.6 filed Aug. 20, 2009. Each of the referenced applications is incorporated herein by reference in its entirety.

FIELD OF THE INVENTION

The present application concerns a method for stabilizing enzymes by storing the enzyme in the presence of a stabilized coenzyme. Additionally or alternatively, the present application concerns an enzyme stabilized with a stabilized coenzyme as well as the use thereof in test elements for detecting analytes.

BACKGROUND

Diagnostic test elements are important components of clinically relevant analytical methods. In this connection, the focus is on the measurement of analytes, for example metabolites or substrates, which for example can be determined directly or indirectly with the aid of an enzyme that is specific for the analyte. In this case, the analytes are converted with the aid of an enzyme-coenzyme complex and subsequently quantified. This entails the analyte to be determined being brought into contact with a suitable enzyme, a coenzyme and optionally a mediator, whereby the coenzyme is physicochemically changed, for example oxidized or reduced, by the enzymatic reaction. If a mediator is additionally used, it usually transfers electrons from the reduced coenzyme released during the conversion of the analyte onto an optical indicator or the conductive components of an electrode so that the process can be detected, by way of non-limiting example, photometrically or electrochemically. A calibration provides a direct relationship between the measured value and the concentration of the analyte to be determined.

An important criterion when providing diagnostic test elements is their long-term stability. Certain test elements known from the prior art which are used in the determination of blood glucose are generally very sensitive to moisture and heat, such that upon exposure to the same the function of the coenzyme and mediator, for example, is usually impaired. Another problem of commercially available test elements is their sensitivity to ambient light where light absorption by the enzyme system can result in damage to the enzyme, coenzyme and/or mediator. In certain instances where, for example, tests are carried out by the end user himself, erroneous results can therefore occur due to an incorrect, unnoticed faulty storage of the measurement system which can be hardly detected by the user and may result in incorrect treatment of the respective disease.

A known measure that can be used to increase the stability of diagnostic test elements is the use of stable enzymes, including for example the use of enzymes from thermophilic organisms. Furthermore, it is possible to stabilize enzymes by chemical modification such as cross-linking, or by mutagenesis. In addition, enzyme stabilizers such as trehalose, polyvinyl pyrrolidone and serum albumin for example, can also be added or the enzymes can be enclosed in polymer networks by photopolymerization for example.

Attempts have also been made to improve the stability of diagnostic test elements by using stable mediators. Thus, the specificity of tests is increased and interferences during the reaction are eliminated by using mediators with a redox potential that is as low as possible. However, the redox potential of the enzyme/coenzyme complexes forms a lower limit for the redox potential of mediators. If the redox potential is lower than this limit, the reaction with the mediators is slowed down or even stopped.

Alternatively, it is also possible to use diagnostic test elements without mediators in which, for example, coenzymes such as the coenzyme NADH are detected directly. A disadvantage of such measurement systems is, however, that native coenzymes such as NAD and NADP are unstable.

NAD and NADP are base-labile molecules whose degradation pathways are described in the literature (N. J. Oppenheimer, in "The Pyridine Nucleotide Coenzyme", Academic Press New York, London 1982, Editor J. Everese, B. Anderson, K. You, chapter 3, pages 56-65). ADP-ribose is mainly formed when NAD or NADP are degraded by cleavage of the glycosyl linkages between the ribose and the pyridine unit. In contrast, the reduced forms NADH and NADPH are acid-labile: for example, epimerization is a known degradation pathway. In both cases, the instability of NAD/NADP and NADH/NADPH is due to the lability of the glycosyl linkage between the ribose unit and the pyridine unit. However, under conditions that are not drastic such as an aqueous solution for example, the coenzymes NAD and NADP are already hydrolyzed solely due to the ambient moisture. This instability may lead to inaccuracies in the measurement of analytes.

A number of NAD/NADP derivatives is described, for example, by B. M. Anderson in "The Pyridine Nucleotide Coenzymes", Academic Press New York, London 1982, editor J. Everese, B. Anderson, K. You, chapter 4. However, most of these derivatives are not well accepted by enzymes. The only derivative that has therefore been used up to now for diagnostic tests is 3-acetylpyridine adenine dinucleotide (acetyl-NAD) which was described for the first time in 1965 (N. O. Kaplan, J. Biol. Chem. (1956), 221, 823). This coenzyme also shows a poor acceptance by enzymes and a change in the redox potential.

International Patent Publication No. WO 01/94370 describes the use of further NAD derivatives with a modified pyridine group. However, modifications of the nicotinamide group generally have a direct influence on the catalytic reaction. In most cases this influence is negative.

In another stabilization concept, the ribose unit was altered in order to thus influence the stability of the glycosyl linkage. This procedure does not directly interfere with the catalytic reaction of the nicotinamide group. However, it may have an indirect influence as soon as the enzyme exhibits a strong and specific binding to the ribose unit. Kaufmann et al. disclose in this connection a number of thioribose-NAD derivatives in International Patent Publication No. WO 98/33936 and U.S. Pat. No. 5,801,006 and in International Patent Publication No. WO 01/49247. However, a relationship between the modification of the nicotinamide ribose unit and the activity of the derivatives in enzymatic reactions has not been shown to date.

carbaNAD, a derivative without a glycosyl linkage was described for the first time in 1988 (J. T. Slama, Biochemistry (1988), 27, 183, and Biochemistry (1989), 28, 7688). The ribose therein is substituted by a carbacyclic sugar unit. Although carbaNAD was described as a substrate for dehydrogenases, its activity has previously not been demonstrated clinically in biochemical detection methods.

A similar approach was described later by G. M. Blackburn (Chem. Comm. (1996), 2765) in order to prepare carbaNAD with a methylene bisphosphonate compound instead of the natural pyrophosphate. The methylene bisphosphonate shows an increased stability towards phosphatases and was used as an inhibitor for ADP-ribosyl cyclase. An increase in hydrolysis stability was not the aim (J. T. Slama, G. M. Blackburn).

International Patent Publication No. WO 2007/012494 and U.S. Pat. No. 7,553,615 finally disclose stabilized NAD/NADH and NADP/NADPH derivatives, enzyme complexes of these derivatives and their use in biochemical detection methods and reagent kits.

One non-limiting object of the present application is to provide a method for stabilizing enzymes, especially for the long-term stabilization of enzymes which at least partially eliminates the above-mentioned disadvantages.

SUMMARY

In one non-limiting aspect, methods for stabilizing an enzyme by storing the enzyme in the presence of a stabilized coenzyme are provided. Still, others aspects include, but are not limited to, an enzyme stabilized with a stabilized coenzyme as well as the use thereof in test elements for detecting analytes.

In one embodiment, a method for stabilizing an enzyme includes storing the enzyme in the presence of a stabilized coenzyme, and the enzyme is selected from the group consisting of an alcohol dehydrogenase (EC 1.1.1.2), a glucose-6-phosphate dehydrogenase (EC 1.1.1.49) and a diaphorase (EC 1.6.99.2).

In another embodiment, a composition includes an enzyme which is stabilized with a stabilized coenzyme. The enzyme exhibits a decrease in enzyme activity of less than 50% based on the initial value of enzyme activity when stored for a period of time of at least 2 weeks in an environment which includes at least one of a temperature of at least 20° C. and a presence of light at a wavelength of ≥300 nm. Further, the enzyme is selected from the group consisting of an alcohol dehydrogenase (EC 1.1.1.2), a glucose-6-phosphate dehydrogenase (EC 1.1.1.49) and a diaphorase (EC 1.6.99.2).

In yet another embodiment, a detection reagent for determining an analyte includes the composition described above. Still, in another embodiment, a test element includes one of this detection reagent and the composition described above.

In another embodiment, a method for stabilizing an enzyme includes storing the enzyme in the presence of a native coenzyme, and the enzyme is a diaphorase (EC 1.6.99.2) or a dehydrogenase selected from the group consisting of an alcohol dehydrogenase (EC 1.1.1.1; EC 1.1.1.2), an L-amino acid dehydrogenase (EC 1.4.1.5), a glucose dehydrogenase (EC 1.1.1.47), a glucose-6-phosphate dehydrogenase (EC 1.1.1.49), a glycerol dehydrogenase (EC 1.1.1.6), a 3-hydroxybutyrate dehydrogenase (EC 1.1.1.30), a lactate dehydrogenase (EC 1.1.1.27; EC 1.1.1.28) and a malate dehydrogenase (EC 1.1.1.37).

Other aspects include unique compositions, methods, techniques, systems and devices involving enzyme stabilization.

Further embodiments, forms, objects, features, advantages, aspects, and benefits shall become apparent from the following description and drawings.

BRIEF DESCRIPTION OF THE DRAWINGS

FIG. 2C is a graphical illustration of the results of the enzyme kinetics of glucose dehydrogenase in the presence of NAD after 5 weeks storage at 32° C. and 85% relative air humidity.

FIG. 21 illustrates amino acid sequences of the glucose dehydrogenase double mutants GlucDH_E96G_E170K (SEQ ID NO: 1) and GlucDH_E170K_K252L (SEQ ID NO: 2).

DETAILED DESCRIPTION

Figure 1A:
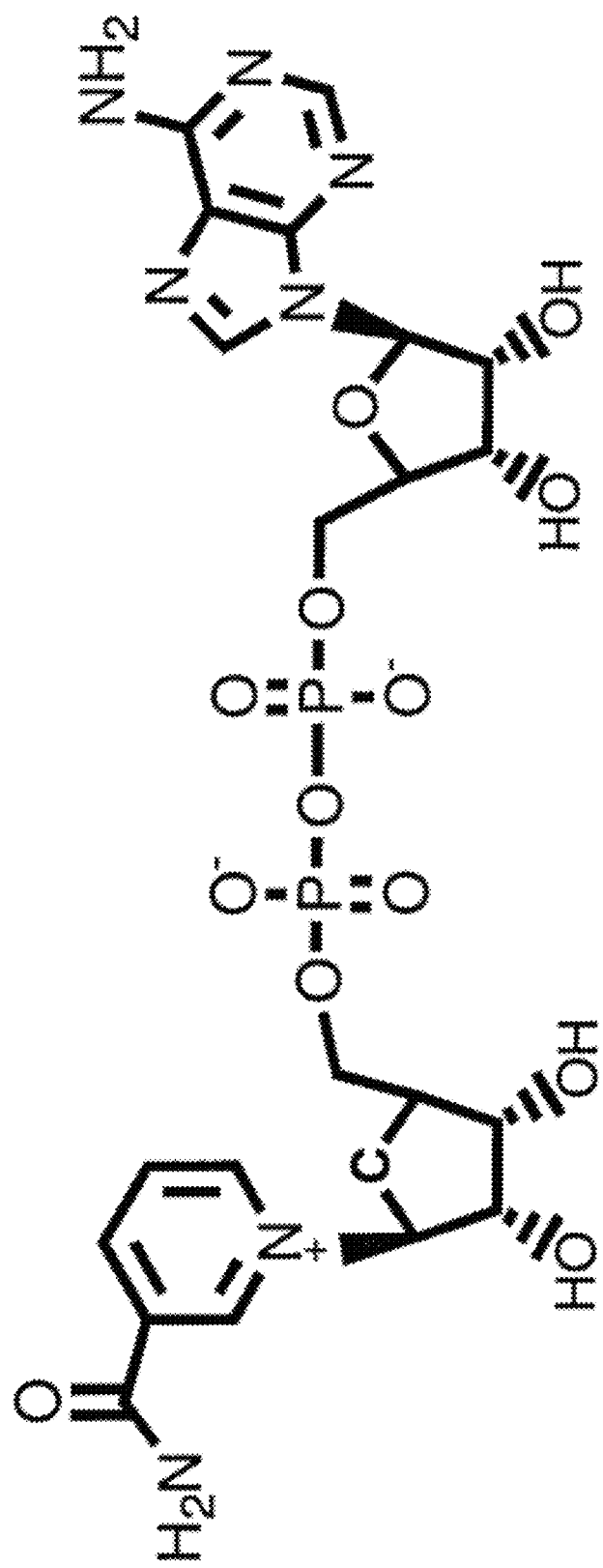
FIG. 1A illustrates the formula of the stabilized coenzyme carbaNAD (cNAD).

In one non-limiting aspect, methods for stabilizing an enzyme by storing the enzyme in the presence of a stabilized coenzyme are provided. Still, others aspects include, but are not limited to, an enzyme stabilized with a stabilized coenzyme as well as the use thereof in test elements for detecting analytes.

It has been surprisingly discovered that a long-term stabilization of an enzyme of several weeks or months at high relative humidity (or even in a liquid phase), at elevated temperatures and in ambient light is possible with the aid of a stabilized coenzyme. In this connection, the term "storage" means that the enzyme is kept for any time period, such as, by way of non-limiting example, a time period of at least 2 weeks, in the presence of the stabilized coenzyme. In one particular form, the storage takes place at atmospheric pressure, room temperature (25° C.) and with a relative air humidity of at least 50%. Other non-limiting time periods for which the enzyme is kept in the presence of the stabilized coenzyme include at least 3 months, at least 6 months, and at least 12 months.

The above-described discovery is surprising because, amongst other reasons, it was previously known that while enzymes exhibit an increased short-term stability of several hours in the presence of the native coenzyme (Bertoldi et al., Biochem. J. (2005), 389, 885; van den Heuvel et al., J. Biol. Chem. (2005), 280, 32115; and Pan et al., J. Chin. Biochem. Soc. (1974), 3, 1), they have a lower stability over a longer period (Nutrition Reviews (1978), 36, 251). The long-term stability towards moisture and/or heat of diagnostic test elements which include an enzyme and a stabilized coenzyme which has now been observed is all the more surprising because stabilized coenzymes have lower binding constants with the enzyme than the corresponding native coenzymes.

In one form, the enzyme stabilized by the methods disclosed herein is a coenzyme-dependent enzyme. Non-limiting examples of such enzymes include, for example, dehydrogenases, including dehydrogenases selected from the group consisting of an alcohol dehydrogenase (EC 1.1.1.1.; EC 1.1.1.2), an L-amino acid dehydrogenase (EC 1.4.1.5), a glucose dehydrogenase (EC 1.1.1.47), a glucose-6-phosphate dehydrogenase (EC 1.1.1.49), a glycerol dehydrogenase (EC 1.1.1.6), a 3-hydroxybutyrate dehydrogenase (EC 1.1.1.30), a lactate dehydrogenase (EC 1.1.1.27; EC 1.1.1.28), a malate dehydrogenase (EC 1.1.1.37) and a sorbitol dehydrogenase. Further non-limiting examples of such enzymes include oxidases such as, for example, glucose oxidase (EC 1.1.3.4) or cholesterol oxidase (EC 1.1.3.6), aminotransferases such as, for example, aspartate aminotransferase or alanine aminotransferase, 5'-nucleotidase, creatine kinase and diaphorase (EC 1.6.99.2). In one particular form, the enzyme is an alcohol dehydrogenase (EC 1.1.1.1; EC 1.1.1.2), a glucose dehydrogenase (EC 1.1.1.47), a glucose-6-phosphate dehydrogenase (EC 1.1.1.49) or a diaphorase (EC 1.6.99.2).

In forms where a glucose dehydrogenase (EC 1.1.1.47) is used as the enzyme, it should be understood that a mutated glucose dehydrogenase can for example be used. As used herein, the term "mutant" refers to a genetically modified variant of a native enzyme which, while having the same number of amino acids, has an amino acid sequence which is modified compared to the wild-type enzyme; i.e., it differs in at least one amino acid from the wild-type enzyme. The introduction of the mutation(s) can take place site-specifically or non-site-specifically. In one particular form, the mutation(s) can take place site-specifically using recombinant methods as known in the specialized field, thereby resulting in at least one amino acid substitution within the amino acid sequence of the native enzyme depending on the respective requirements and conditions. In one particular form, the mutant enzyme has an increased thermal or hydrolytic stability compared to the wild-type enzyme. Non-limiting examples of such mutants are described by Baik (Appl. Environ. Microbiol. (2005), 71, 3285), Vásquez-Figueroa (ChemBioChem. (2007), 8, 2295) as well as in International Patent Publication No. WO 2005/045016 A2 to Krebber et al., the disclosure of which is hereby incorporated herein by reference in its entirety.

In one form, a mutated glucose dehydrogenase can in principle contain the amino acid(s) which is(are) modified compared to the corresponding wild-type glucose dehydrogenase at any position in its amino acid sequence. In more particular forms, the mutated glucose dehydrogenase contains a mutation in at least one of the positions 96, 170 and 252 of the amino acid sequence of the wild-type glucose dehydrogenase. In another particular form, the mutated glucose dehydrogenase has mutations at position 96 and position 170. In still another more particular form, the mutated glucose dehydrogenase has mutations at position 170 and position 252. In addition, it should be understood that, in certain forms, it is advantageous for the mutated glucose dehydrogenase to contain no further mutations apart from those discussed above.

The mutation at positions 96, 170 and 252 can in principle comprise any amino acid substitution which results in a stabilization such as, for example, an increase in the thermal or hydrolytic stability, of the wild-type enzyme. In one form, the mutation at position 96 includes an amino acid substitution of glutamic acid by glycine, whereas in relation to position 170 an amino acid substitution of glutamic acid by arginine or lysine is present. In one particular form, an amino acid substitution of glutamic acid by lysine at position 170 is present. With regard to the mutation at position 252, it may include, by way of non-limiting example, an amino acid substitution of lysine by leucine.

The mutated glucose dehydrogenase can be obtained by mutation of a wild-type glucose dehydrogenase derived from any biological source, where the term "biological source" as used herein includes both prokaryotes such as, for example, bacteria, and eukaryotes such as, for example, mammals and other animals. In one form, the wild-type glucose dehydrogenase is derived from a bacterium. In more particular forms, a glucose dehydrogenase is derived from *Bacillus megaterium, Bacillus subtilis* or *Bacillus thuringiensis*. In one particular form, a glucose dehydrogenase is derived from *Bacillus subtilis*.

In one particular embodiment, the mutated glucose dehydrogenase is a glucose dehydrogenase obtained by mutation of wild-type glucose dehydrogenase from *Bacillus subtilis* which has the amino acid sequence shown in SEQ ID NO:1 (GlucDH_E96G_E170K) or that shown in SEQ ID NO:2 (GlucDH_E170K_K252L).

A stabilized coenzyme within the scope of the present application is a coenzyme which has been chemically modified compared to the native coenzyme and which at atmospheric pressure has a higher stability compared to the native coenzyme towards moisture, temperatures, in particular those in the range from 0° C. to 50° C., acids and bases, in particular those in the range from pH 4 to pH 10, and/or nucleophiles such as, for example, alcohols or amines. Similarly, in this respect it should be understood that the stabilized coenzyme can exhibit its activity under identical environmental conditions over a longer time period than the native coenzyme. In one form, the stabilized coenzyme has a higher hydrolytic stability compared to the native coenzyme. In another particular form, the stabilized coenzyme has a complete hydrolytic stability under the test conditions compared to the native coenzyme. In comparison with the native coenzyme, the stabilized coenzyme may have a reduced binding constant for the enzyme such as, for example, a binding constant reduced by a factor of two or more.

More particular but non-limiting examples of stabilized coenzymes include stabilized derivatives of nicotinamide adenine dinucleotide (NAD/NADH) or nicotinamide adenine dinucleotide phosphate (NADP/NADPH) or shortened NAD derivatives; for example, those without the AMP moiety or with non-nucleoside residues such as, for example, hydrophobic residues. In one particular form, the compound of formula (I) is used as a stabilized coenzyme.

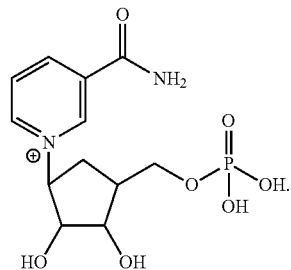

(I)

More particular but non-limiting examples of stabilized derivatives of NAD/NADH and NADP/NADPH are described in the aforementioned references, the disclosures of which are incorporated herein by reference in their entirety. Stabilized coenzymes are also described in International Patent Publication No. WO 2007/012494 and U.S. Pat. No. 7,553,615, the disclosures of which references are hereby incorporated herein by reference in their entirety. In one form, the stabilized coenzyme is selected from compounds of the general formula (II):

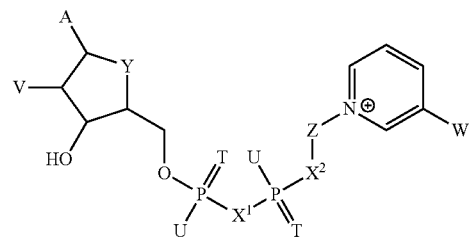

(II)

in which
A=adenine or an analogue thereof;
T=in each case independently denotes O or S;
U=in each case independently denotes OH, SH, $BH_3^-$, or $BCNH_2^-$;
V=in each case independently denotes OH or a phosphate group, or two groups which form a cyclic phosphate group;
W=COOR, $CON(R)_2$, COR, or $CSN(R)_2$ in which R in each case independently denotes H or a $C_1$-$C_2$ alkyl;
$X^1$, $X^2$=in each case independently denote O, $CH_2$, $CHCH_3$, $C(CH_3)_2$, NH, or $NCH_3$;
Y=NH, S, O, or $CH_2$;
Z=a linear or cyclic organic residue;
provided that Z and the pyridine residue are not linked by a glycosidic bond, or a salt or optionally a reduced form thereof.

In certain forms, Z in the compounds of formula (II) is a linear residue with 4-6 C atoms, and in one particular form with 4 C atoms, in which 1 or 2 C atoms are optionally replaced by one or more heteroatoms selected from O, S and N, or a residue comprising a cyclic group with 5 or 6 C atoms which optionally contains a heteroatom selected from O, S and N as well as optionally one or more substituents, and a residue $CR^4_2$, where $CR^4_2$ is bound to the cyclic group and to $X^2$, where $R^4$ in each case independently denotes H, F, Cl, or $CH_3$.

In one particular form, Z is a saturated or unsaturated carbocyclic or heterocyclic 5-membered ring and more particularly but not exclusively is a compound of the general formula (III)

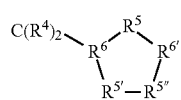

(III)

in which a single or double bond may be present between $R^{5'}$ and $R^{5''}$, where
$R^4$=in each case independently denotes H, F, Cl, or $CH_3$;
$R^5=CR^4_2$;
$R^{5'}$=O, S, NH, $NC_1$-$C_2$-alkyl, $CR^4_2$, CHOH, or $CHOCH_3$, and $R^{5''}=CR^4_2$, CHOH, or $CHOCH_3$ if there is a single bond between $R^{5'}$ and $R^{5''}$;
$R^{5'}=R^{5''}=CR^4$ if there is a double bond between $R^{5'}$ and $R^{5''}$ and
$R^6$, $R^{6'}$=in each case independently denote CH or $CCH_3$.

In one embodiment, the compounds described herein contain adenine or adenine analogues such as, for example, $C_8$-substituted and $N_6$-substituted adenine, deaza variants such as 7-deaza, aza variants such as 8-aza or combinations such as 7-deaza or 8-aza or carbocyclic analogues such as formycin where the 7-deaza variants can be substituted in the 7 position by halogen, $C_1$-$C_6$ alkinyl, $C_1$-$C_6$ alkenyl or $C_1$-$C_6$ alkyl.

In a further embodiment, the compounds of formula (II) contain adenosine analogues which contain for example 2-methoxydeoxyribose, 2'-fluorodeoxyribose, hexitol, altritol or polycyclic analogues such as bicyclo, LNA and tricyclo sugars instead of ribose.

In particular forms (di)-phosphate oxygens can also be isotronically replaced in the compounds of formula (II) such as, for example, $O^-$ by $S^-$ or $BH_3^-$, O by NH, $NCH_3$ or $CH_2$, and =O by =S. In particular but non-limiting forms, W in the compounds of formula (II) described herein is $CONH_2$ or $COCH_3$.

Figure 1B:
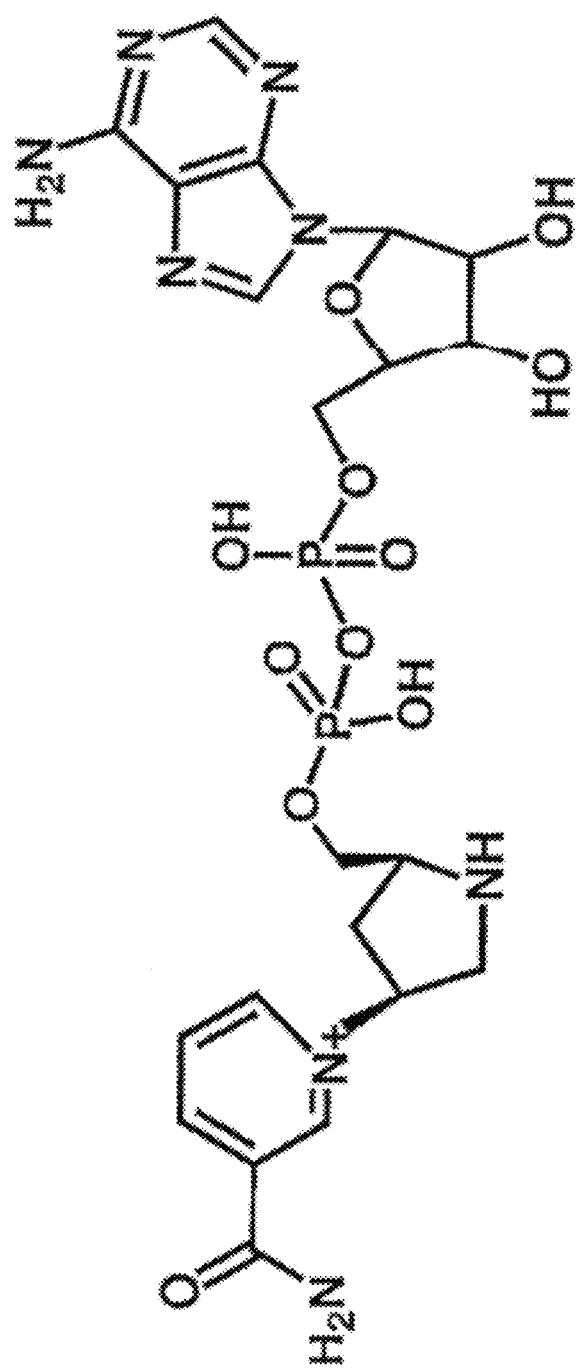
FIG. 1B illustrates the formula of the stabilized coenzyme pyrrolidinyl NAD.

In one form, $R^5$ in the groups of formula (III) is $CH_2$. Furthermore, in one form $R^{5'}$ is selected from $CH_2$, CHOH and NH. In a particular embodiment, $R^{5'}$ and $R^{5''}$ are each CHOH. In yet another particular embodiment, $R^{5'}$ is NH and $R^{5''}$ is $CH_2$. One specific embodiment includes a compound of formula (III) in which $R^4$=H, $R^5=CH_2$, $R^{5'}=R^{5''}$=CHOH and $R^6=R^{6'}$=CH. Specific but non-limiting examples of particular stabilized coenzymes are shown in FIGS. 1A and 1B. In one particular embodiment, the stabilized coenzyme is the compound carbaNAD.

In one aspect, the method disclosed herein is especially suitable for the long-term stabilization of enzymes. This means that the stabilized enzyme is stored, for example, as a dry substance or in a liquid phase, for example over a period of at least 2 weeks, of at least 4 weeks or of at least 8 weeks during which the enzyme activity decreases by less than 50%, by less than 30%, or by less than 20% based on the initial value of the enzyme activity.

The method disclosed herein additionally includes a storage of the stabilized enzyme at elevated temperatures, for example at a temperature of at least 20° C., of at least 25° C. or of at least 30° C. during which the enzyme activity decreases by less than 50%, by less than 30% or by less than 20% based on the initial value of the enzyme activity. The storage can, if necessary, be carried out for a longer period as stated above.

Moreover, the method disclosed herein envisages a storage of the stabilized enzyme in the presence of ambient light, i.e. in the presence of light at a wavelength of ≥300 nm, during which the enzyme activity decreases by less than 50%, by less than 30% or by less than 20% based on the initial value of the enzyme activity. In this case the storage can, if necessary, be carried out for a longer period and/or at elevated temperatures as stated above. Due to the stability of the enzyme system towards ambient light, the stabilized enzyme can in addition also be exposed to direct sunlight shortly before use and/or after removal from a package.

The stabilization techniques described herein also enable the stabilized enzyme to be stored without a desiccant and/or at a high relative air humidity; for example, at a relative air humidity of at least 50%, during which the enzyme activity decreases by less than 50%, by less than 30% or by less than 20% based on the initial value of the enzyme activity. In this case the storage can, if necessary, be carried out for a longer period, at elevated temperatures and/or in the presence of ambient light as stated above. Methods or tests for determining the activity of enzymes are widely known in the prior art and, if required, can be adapted by a person skilled in the art to the respective requirements where the same test conditions are used in each case to compare the enzyme activity before and after storage.

The stabilized enzyme can be stored on the one hand as a dry substance and, on the other hand, in a liquid phase. In one particular form, the stabilized enzyme is stored on or in a test element that is suitable for determining an analyte. In this case the stabilized enzyme is, for example, a component of a detection reagent which can optionally contain other components such as mediators, optical indicators, salts, buffers, etc.

The stabilized enzyme can be used, by way of non-limiting, to detect analytes for example parameters in body fluids, such as blood, serum, plasma or urine or in samples of sewage or in foods. Any biological or chemical substances that can be detected by a redox reaction can be determined as analytes; for example, substances that are substrates of a coenzyme-dependent enzyme or coenzyme-dependent enzymes themselves. More particular but non-limiting examples of analytes are glucose, lactic acid, malic acid, glycerol, alcohol, cholesterol, triglycerides, ascorbic acid, cysteine, glutathione, peptides, urea, ammonium, salicylate, pyruvate, 5'-nucleotidase, creatine kinase (CK), lactate dehydrogenase (LDH), carbon dioxide, etc. In one particular form, the analyte is glucose.

Another aspect of the present application is the use of a compound described herein or of an enzyme stabilized according to the methods described herein to detect an analyte in a sample by means of an enzymatic reaction which, in one particular form, includes the detection of glucose with the aid of a glucose dehydrogenase (EC 1.1.1.47) or a glucose-6-phosphate dehydrogenase (EC 1.1.1.49) using suitable coenzymes.

The change in the stabilized coenzyme caused by reaction with the analyte can in principle be detected in any way. In this case it is in principle possible to utilize all methods known from the prior art for detecting enzymatic reactions. However, in one particular form, the change in the coenzyme is detected by optical methods. Optical detection methods include, for example, the measurement of absorption, fluorescence, circular dichroism (CD), optical rotation dispersion (ORD), or refractometry.

Optical detection methods which are used in particular forms of the present application include photometry and fluorimetry. In order to photometrically measure a change in the coenzyme due to reaction with the analyte it is, however, additionally necessary for at least one mediator to be present which increases the reactivity of the reduced coenzyme and enables electrons to be transferred to a suitable optical indicator or an optical indicator system.

Mediators which are suitable for the purposes of the present application include, among others, nitrosoanilines such as for example [(4-nitrosophenyl)imino]-dimethanol hydrochloride, quinones such as for example phenanthrene quinones, phenanthroline quinones or benzo[h]-quinoline quinones, phenazines such as 1-(3-carboxypropoxy)-5-ethylene phenazinium trifluoromethane sulfonate and/or diaphorase (EC 1.6.99.2).

Diaphorases, especially when compared with phenazines, have a higher stability, but their function can be impaired by degradation products of native coenzymes, for example, by degradation products of NAD or NADP as known, for example, from DE 2 061 984 A.

Non-limiting examples of phenanthroline quinones include 1,10-phenanthroline-5,6-quinones, 1,7-phenanthroline-5,6-quinones, 4,7-phenanthroline-5,6-quinones as well as N-alkylated and N,N'-dialkylated salts thereof, where in the case of N-alkylated or N,N'-dialkylated salts, halogenides, trifluoromethane sulfonate or other anions that increase the solubility may be preferred as the counterion. Diaphorases which are particularly suitable for the purposes of the present application include, but are not limited to, diaphorase from porcine heart, *Clostridium kluyverii* and *Bacillus stearothermophilus* as well as the diaphorase mutant described in U.S. Patent Publication No. 2007/0196899A1 (the contents of which are hereby incorporated herein by reference in their entirety), which have an improved catalytic function and thermostability compared to native diaphorases.

Any substance which is reducible and undergoes a detectable change in its optical properties such as, for example, colour, fluorescence, reflectance, transmission, polarization and/or refractive index can be used as an optical indicator or as an optical indicator system. The determination of the presence and/or the amount of the analyte in the sample can be carried out with the naked eye and/or by means of a detection device using a photometric method that appears suitable to a person skilled in the art. Heteropoly acids and, in particular 2,18-phosphomolybdic acid, may be used as optical indicators which are reduced to the corresponding heteropoly blue. Alternatively, it is also possible to use quinones such as, for example, resazurine, dichlorophenol indophenol and/or tetrazolium salts as optical indicators. Tetrazolium salts which are particularly suitable for the purpose of the present application include, but are not limited to, the commercially available products WST-3, WST-4 and WST-5 (all from the Dojindo Company).

In one particular form, the change in the coenzyme is detected by measuring the fluorescence. Fluorescence measurement is highly sensitive and enables even low concentrations of the analyte to be detected in miniaturized systems. Alternatively, the change in the coenzyme can also be detected electrochemically using a suitable test element such as, for example, an electrochemical test strip. The precondition for this is once again the use of suitable mediators which can be converted by the reduced coenzyme into a reduced form by transfer of electrons. The analyte is determined by measuring the current which is needed to reoxidize the reduced mediator which correlates with the concentration of the analyte in the sample. Non-limiting examples of mediators which can be used for electrochemical measurements include the mediators described above for use for photometric measurements.

It is possible to use a liquid test to detect an analyte where the reagent is, for example, present in the form of a solution or suspension in an aqueous or non-aqueous liquid, or as a powder or lyophilisate. However, it is also possible to use a dry test where the reagent is applied to a support. The support can, for example, be a test strip comprising an absorbent and/or swellable material which is wetted by the sample liquid to be investigated.

One particular test format includes the use of the enzyme glucose-6-phosphate dehydrogenase with a stabilized NAD derivative for the detection of glucose especially in a wet test in which case a derivative of the reduced coenzyme NADH is formed. NADH is detected by optical methods, for example by photometric or fluorometric determination, after UV excitation. Another particular test system is described in U.S. Patent Publication No. 2005/0214891, the contents of which are hereby incorporated herein by reference in their entirety.

A further aspect of the present application concerns an enzyme stabilized with a stabilized coenzyme where the stabilized enzyme exhibits a decrease in enzyme activity of less than 50%, less than 30% or less than 20% based on the initial value of enzyme activity when stored for at least 2 weeks, at least 4 weeks or at least 8 weeks at a temperature of at least 20° C., at least 25° C. or at least 30° C. and/or in the presence of light at a wavelength of ≥300 nm, where appropriate at high air humidity and/or in the absence of desiccants. In this case an enzyme is used as described above.

Yet a further aspect of the present application concerns a detection reagent for determining an analyte which contains a stabilized enzyme as described above. In yet another aspect, a test element contains an enzyme stabilized according to the disclosure provided herein or a detection reagent described herein. The detection reagent and the test element may be suitable for carrying out dry tests or liquid tests. In one form, the test element is a test strip for the fluorometric or photometric detection of an analyte. Such a test strip contains the stabilized enzyme in an immobilized form on an absorbent and/or swellable material such as cellulose, plastic, etc.

Yet a further aspect of the present application concerns a method for stabilizing an enzyme especially towards ambient light, wherein the enzyme as previously specified, is stored in the presence of a native coenzyme. In one particular form, an alcohol dehydrogenase (EC 1.1.1.1; EC 1.1.1.2), a glucose dehydrogenase (EC 1.1.1.47), a glucose-6-phosphate dehydrogenase (EC 1.1.1.49) or a diaphorase (EC 1.6.99.2) is used as the enzyme. In other forms, the enzyme is a glucose dehydrogenases (EC 1.1.1.47), including native and mutated glucose dehydrogenases, or a glucose-6-phosphate dehydrogenases (EC 1.1.1.49). A native nicotinamide adenine dinucleotide (NAD/NADH) or a native nicotinamide adenine dinucleotide phosphate (NADP/NADPH) compound is used as the native coenzyme. In one particular form, native NAD or NADP is used as the native coenzyme.

EXAMPLES

The following examples are for illustration purposes and are not to be construed as limiting the invention disclosed in this document to only the embodiments disclosed in these examples.

Example 1 carbaNAD (FIG. 1A) or NAD were added to the glucose-specific GlucDH. These formulations were each applied to Pokalon foils (Lonza) and, after drying, stored under warm and humid conditions (32° C., 85% relative air humidity). Subsequently, the reaction kinetics and the function curve were determined at regular intervals. In parallel at each of the measurement times a cNAD/NAD analysis and a determination of the residual activity of the enzyme were carried out.

Figure 2A:
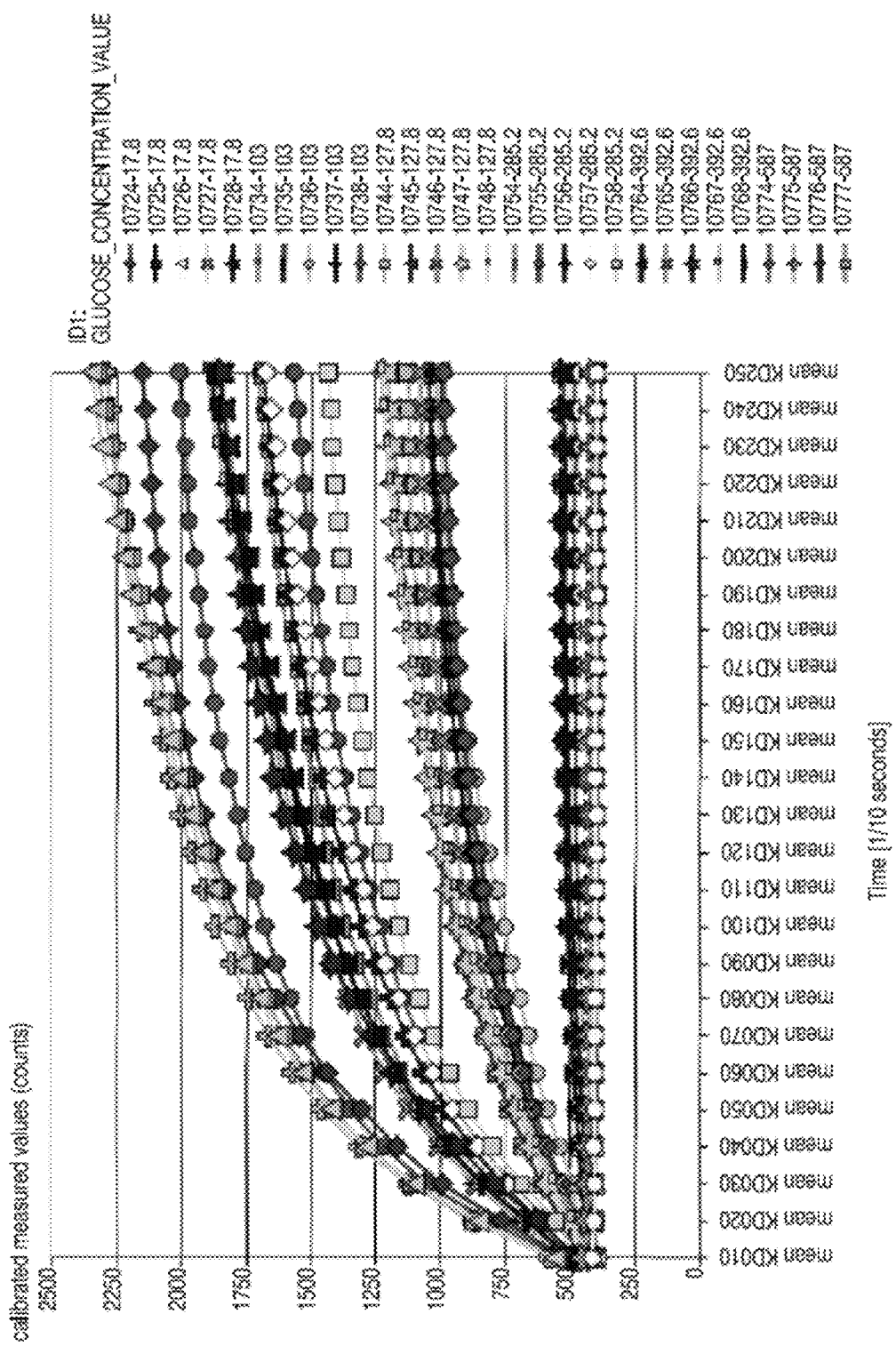
FIG. 2A is a graphical illustration of the results of the enzyme kinetics of glucose dehydrogenase in the presence of NAD after 1 day.
Figure 2B:
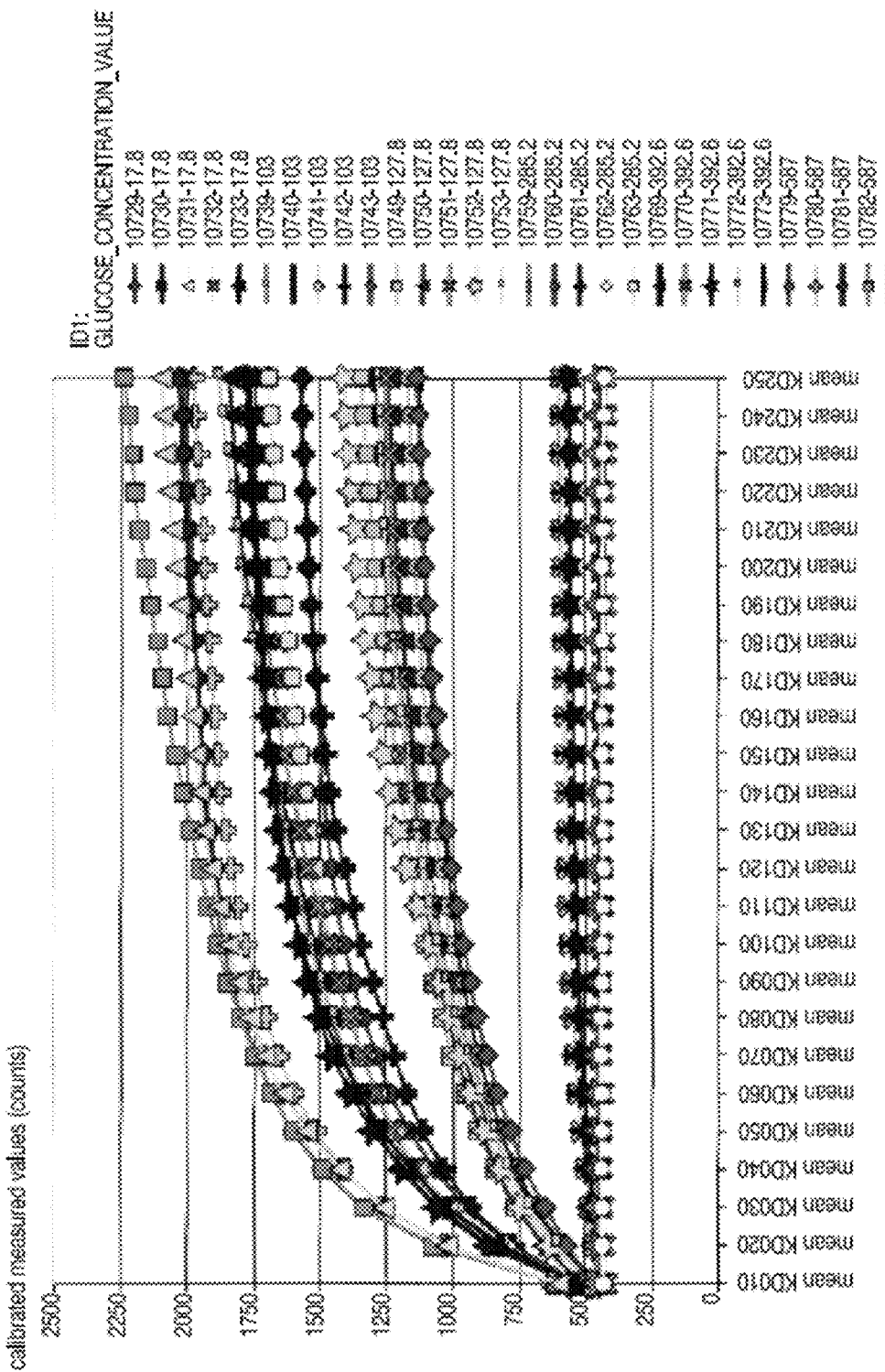
FIG. 2B is a graphical illustration of the results of the enzyme kinetics of glucose dehydrogenase in the presence of cNAD after 1 day.
Figure 2D:
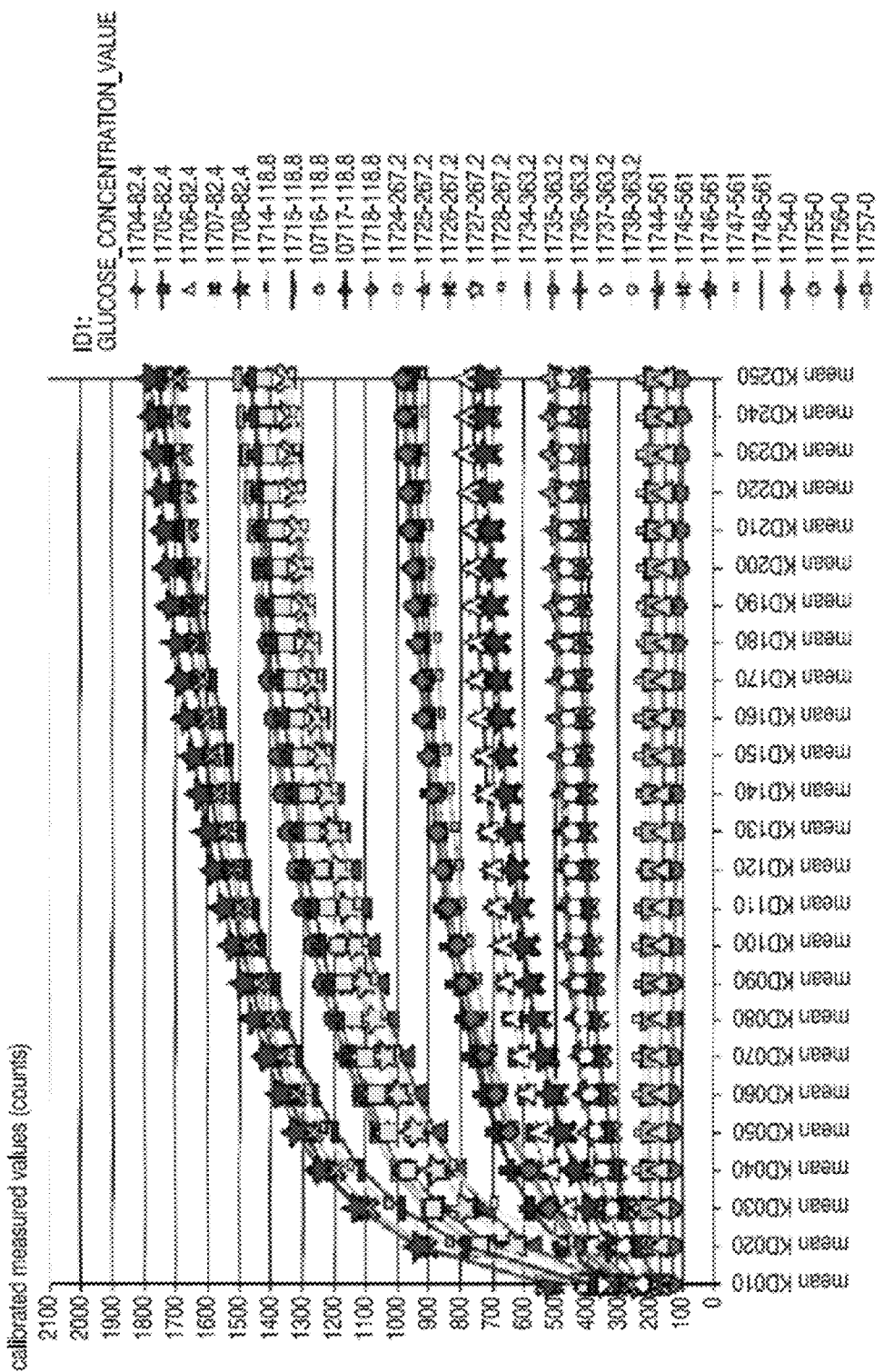
FIG. 2D is a graphical illustration of the results of the enzyme kinetics of glucose dehydrogenase in the presence of cNAD after 5 weeks storage at 32° C. and 85% relative air humidity.

The kinetics curves for NAD (FIG. 2A) and cNAD (FIG. 2B) determined on the first day are comparable and also show a similar increase in the glucose dependency. However, a significant difference in the kinetics curves can be seen after 5 weeks. Whereas there is a major decrease in the dynamic range of the kinetics for NAD (FIG. 2C), the kinetics of the enzyme stabilized with cNAD remains virtually unchanged (FIG. 2D).

Figure 3:
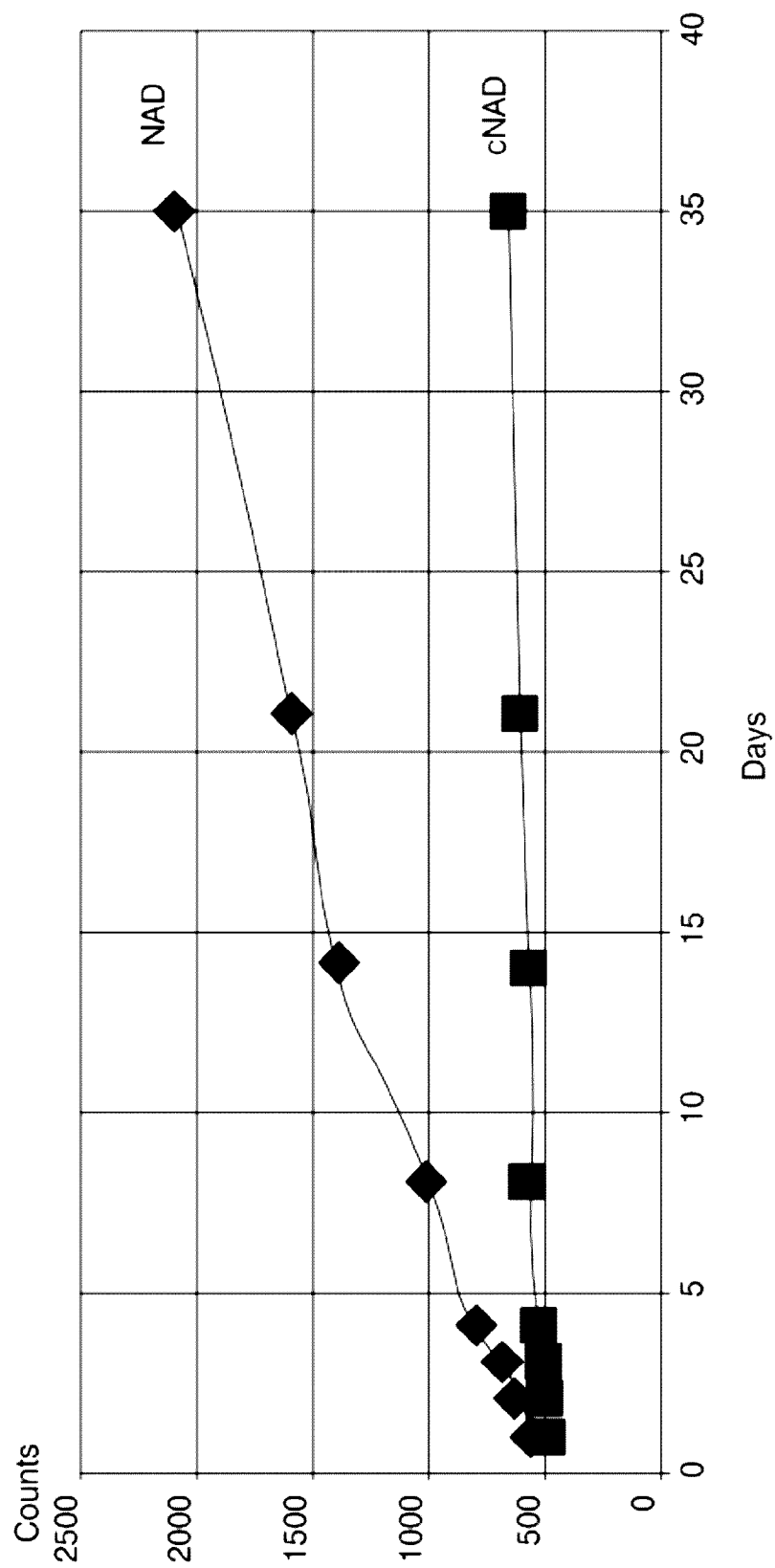
FIG. 3 illustrates a graphical comparison of the blank values of glucose dehydrogenase in the presence of NAD or of GlucDH in the presence of cNAD over a period of up to 5 weeks at 32° C. and 85% air humidity.

There is also a considerable difference in the blank values (dry blank value before application of a blood sample) as shown in FIG. 3. The increase in the dry blank value for NAD is due to the formation of fluorescent particles (Oppenheimer (1982), Supra). Surprisingly this does not occur with cNAD.

Figure 4:
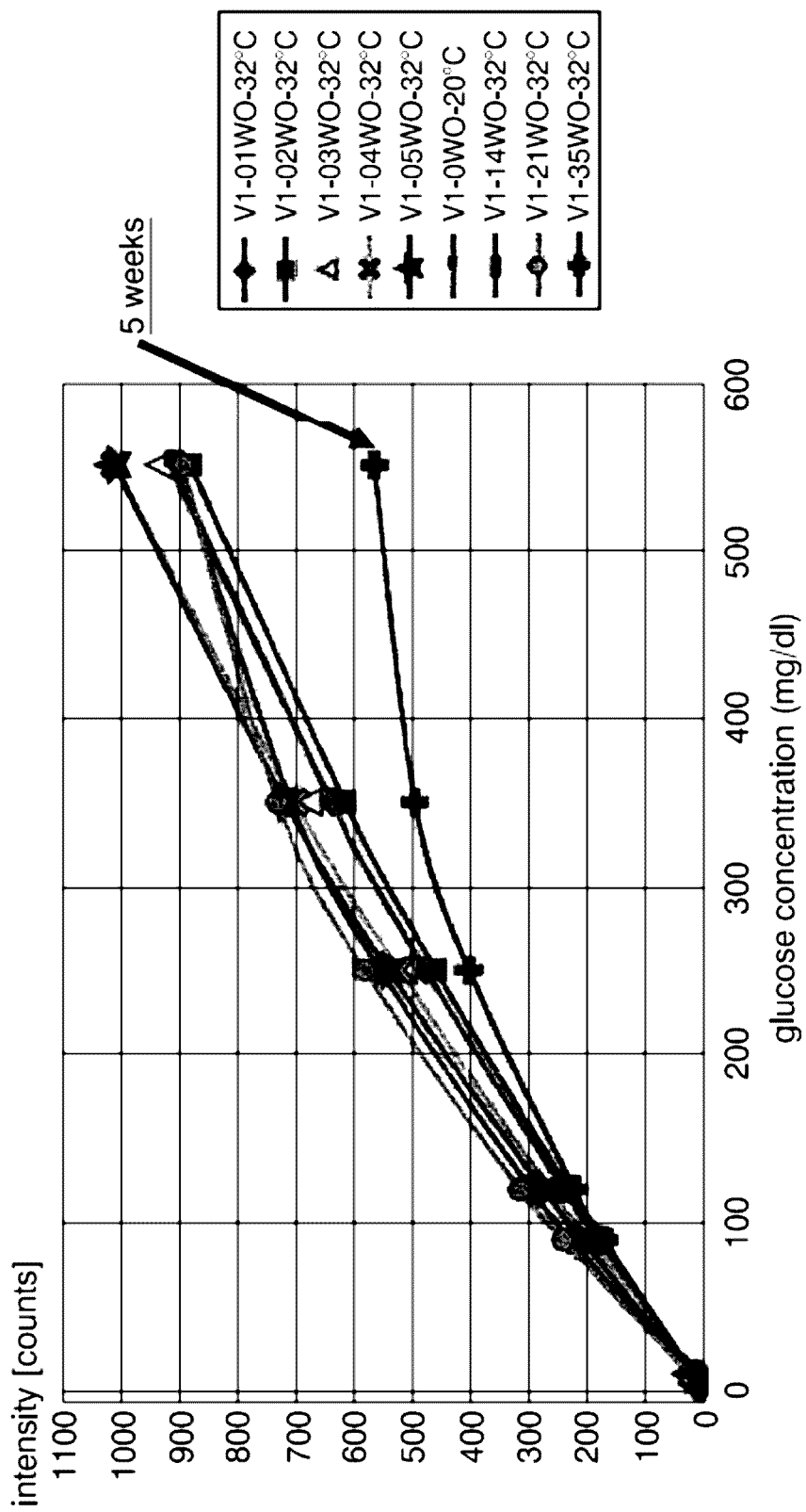
FIG. 4 is a graphical illustration of various function curves of glucose dehydrogenase after storage of glucose dehydrogenase in the presence of NAD at 32° C. and 85% air humidity for periods between 1 day and 5 weeks.
Figure 5A:
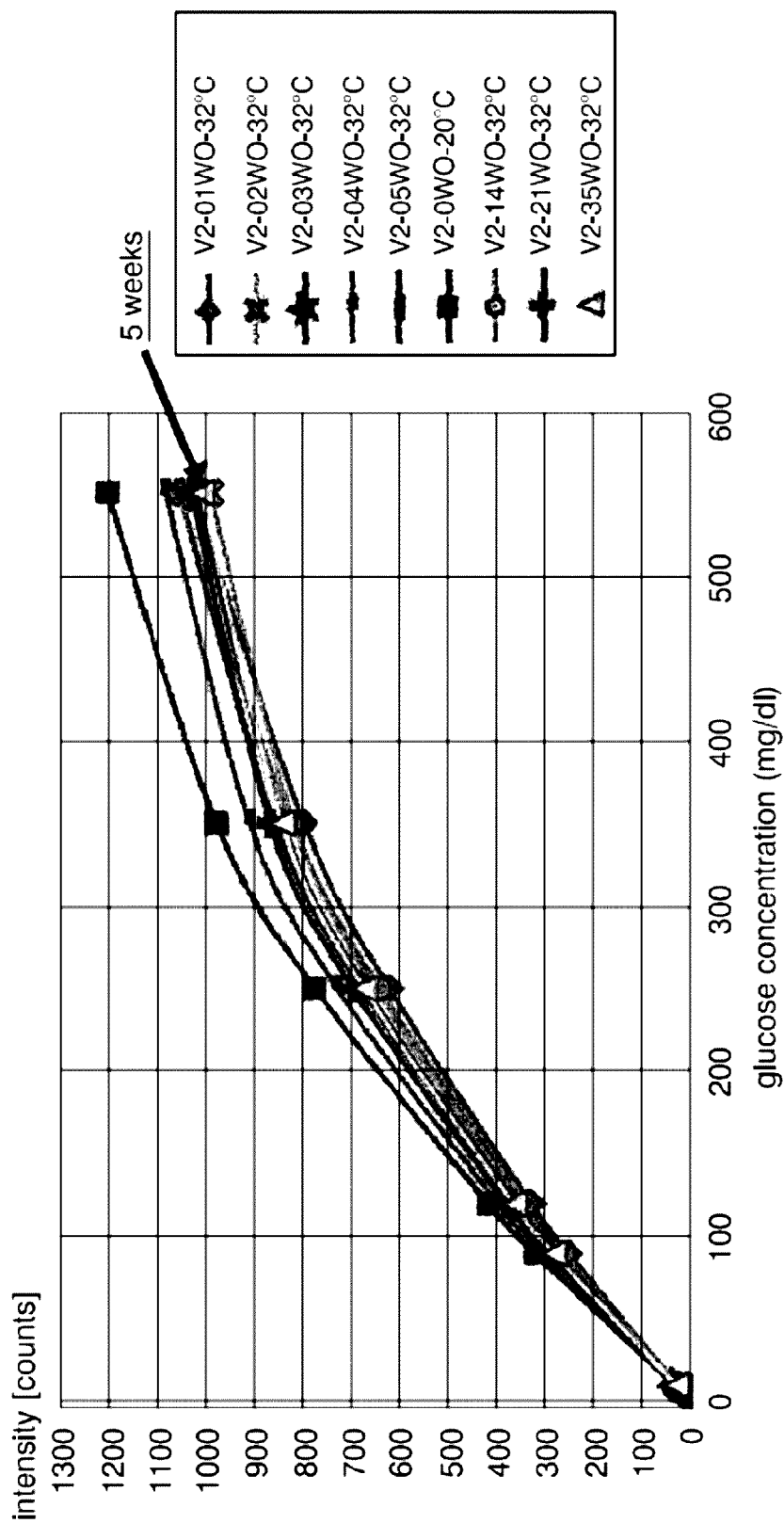
FIGS. 5A and 5B are graphical illustrations of various function curves of glucose dehydrogenase after storage of glucose dehydrogenase in the presence of cNAD at 32° C. and 85% air humidity for periods between 1 day and 5 weeks (FIG. 5A) and between 1 day and 24 weeks (FIG. 5B).
Figure 5B:
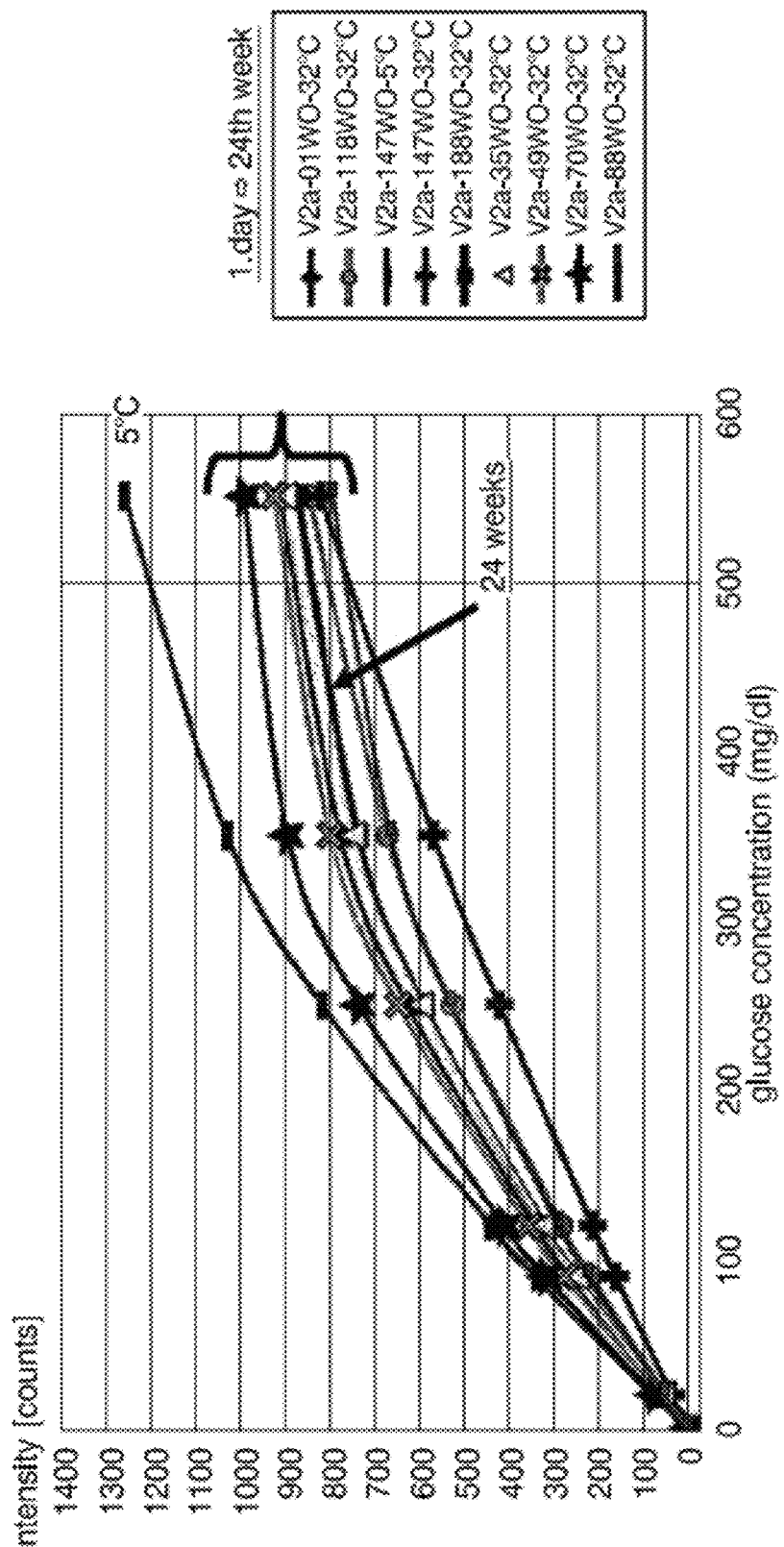

The different stability of glucose dehydrogenase in the presence of NAD or cNAD is also evident from a comparison of FIGS. 4 and 5. After 5 weeks the function curve for the enzyme stabilized with cNAD still lies within the set of curves of the previous measurements (FIG. 5A), whereas the curve for the enzyme treated with NAD (FIG. 4) shows a fall-off at higher concentrations which is a typical sign for inadequate amounts of enzyme/coenzyme. FIG. 5B shows various function curves of the glucose dehydrogenase stabilized with cNAD over a period of 24 weeks. In this connection it is clear that the function of the enzyme is only slightly changed at high glucose concentrations over the entire period and approximately corresponds after 24 weeks to the value obtained after 5 weeks.

Figure 6:
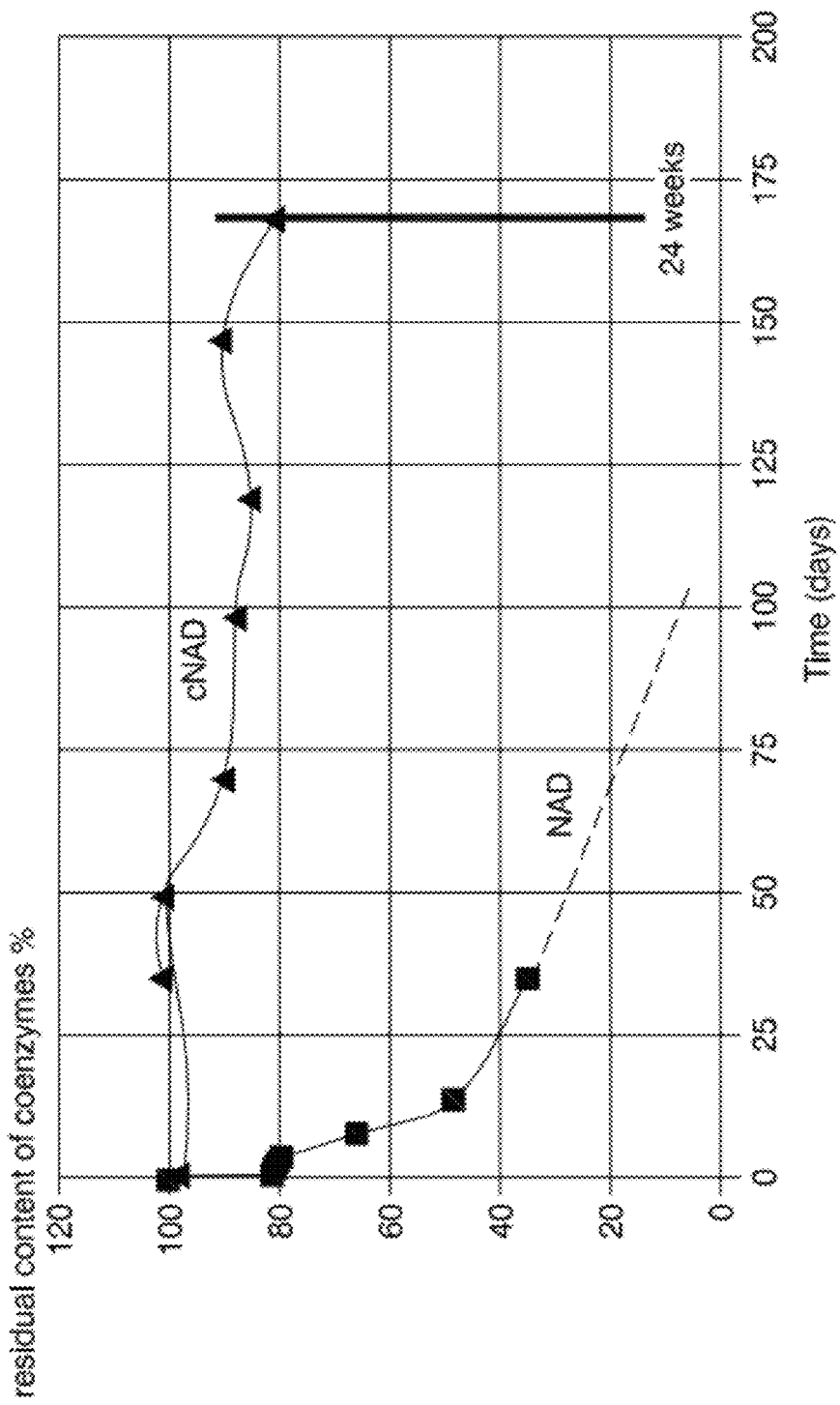
FIG. 6 is a graphical illustration of the residual content of NAD or cNAD after storage of glucose dehydrogenase in the presence of NAD or cNAD respectively for 24 weeks at 32° C. and 85% air humidity.

The relation between the structure of the coenzyme and its stability over a predetermined period is shown in FIG. 6. According to this the residual content of cNAD in a glucose detection reagent is still about 80% of the initial value after 24 weeks storage (at 32° C. and 85% relative air humidity), whereas the content of NAD in a glucose detection reagent stabilized with NAD is already reduced to about 35% of the initial value after 5 weeks and, by extrapolation, is reduced to zero after about 17 weeks.

Figure 7A:
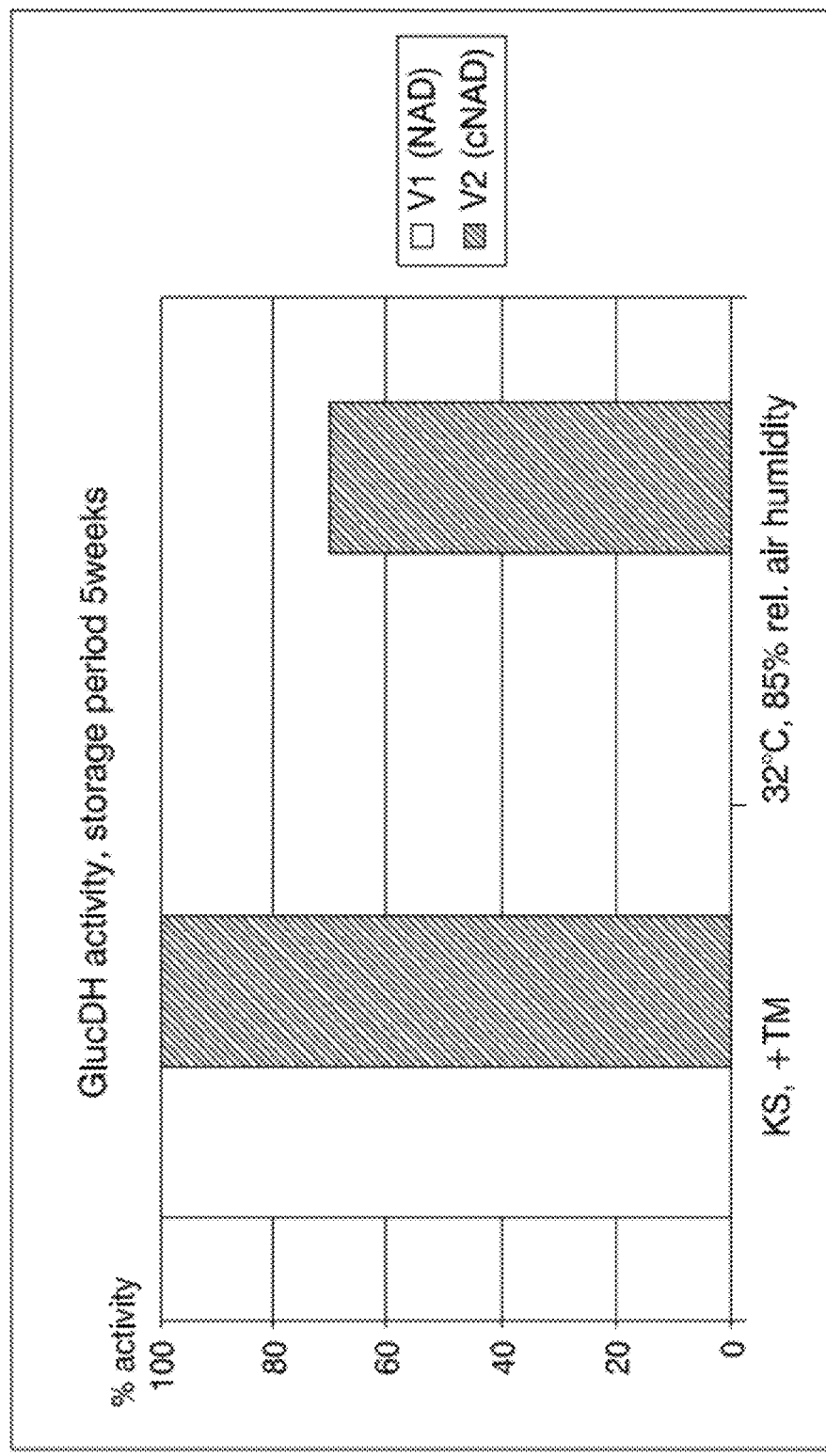
FIGS. 7A and 7B are graphical illustrations of the GlucDH activity after storage of glucose dehydrogenase in the presence of NAD or cNAD for 5 weeks (FIG. 7A) or 24 weeks (FIG. 7B) at 32° C. and 85% air humidity.
Figure 7B:
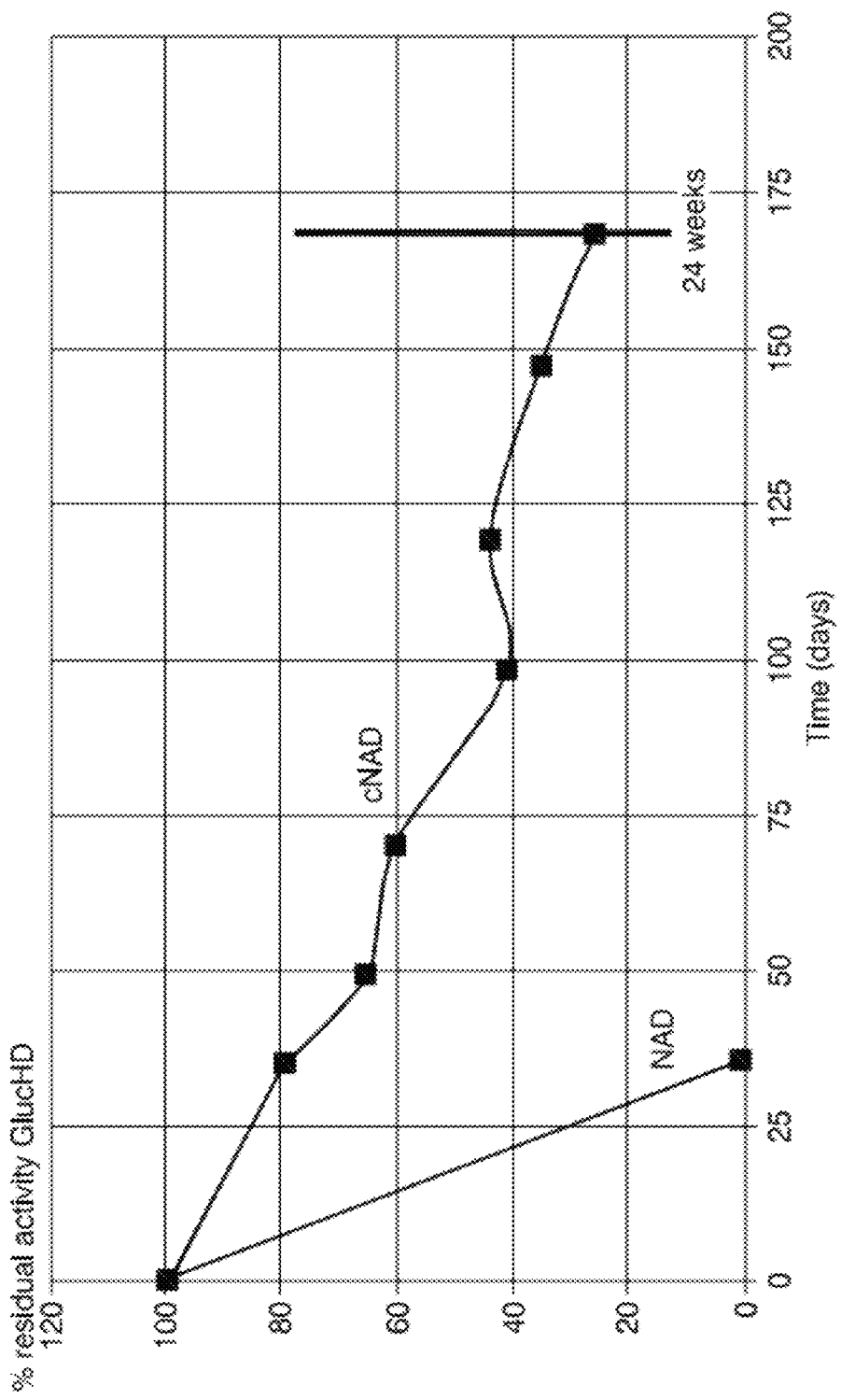

The result of the determination of residual activity of the active enzyme GlucDH after 5 weeks at 32° C. and 85% relative air humidity (FIG. 7A) is completely surprising. The enzyme stabilized with NAD now only has an extremely low enzyme activity (0.5%), whereas the enzyme stabilized with cNAD still has a residual activity of 70% (in each case compared to the samples stored in a refrigerator (KS) with desiccant (TM)). After 24 weeks at 32° C. and 85% relative air humidity (FIG. 7B) the residual activity of the enzyme when stabilized with cNAD is still about 25%.

Figure 8:
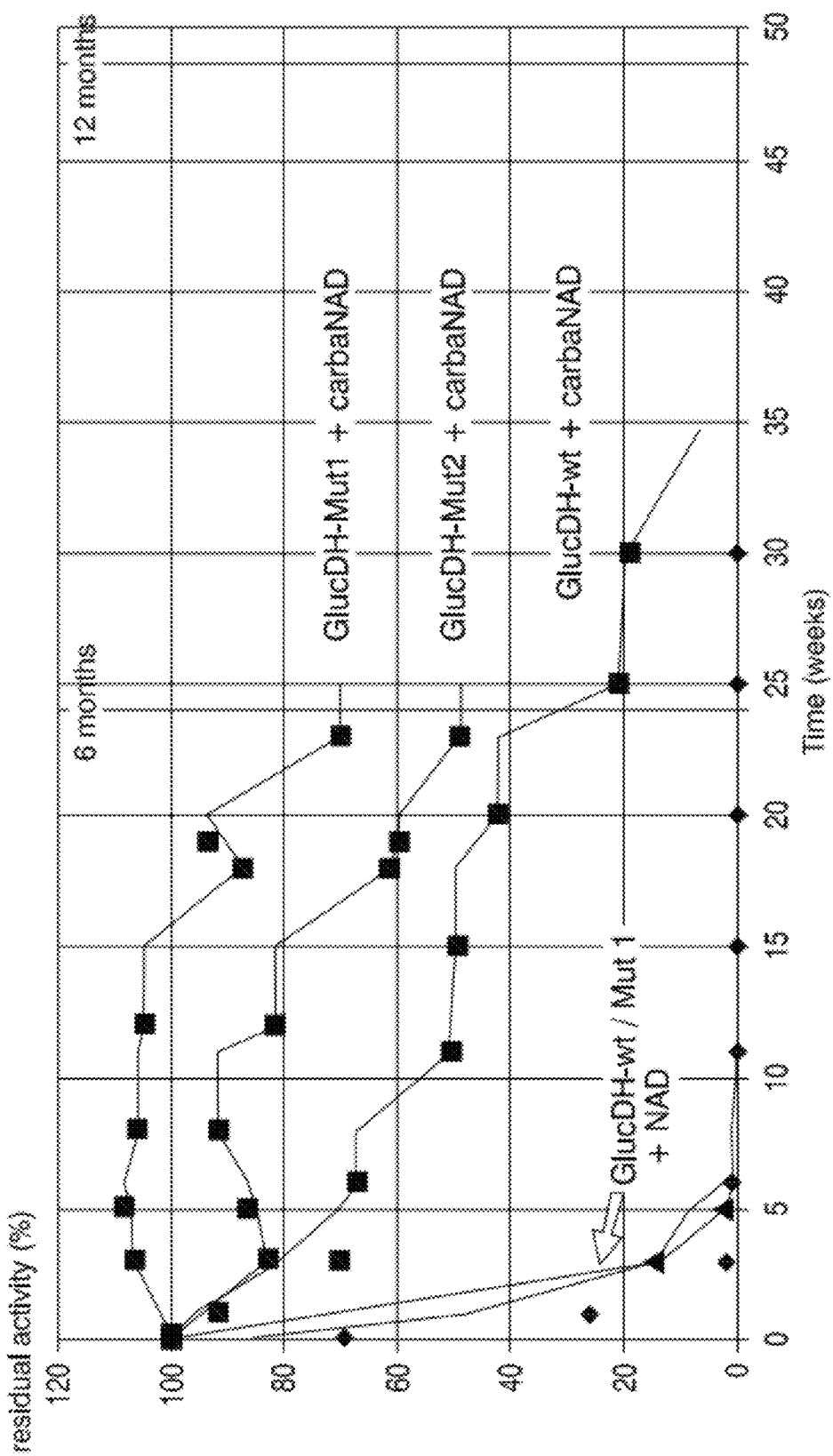
FIG. 8 is a graphical illustration of the GlucDH activity after storage of glucose dehydrogenase (GlucDH-wt), the double mutant GluceDH_E96G_E170K (GlucDH-Mut1) and the double mutant GlucDH_E170K_K252L (GlucDG-Mut2) for a period of 25 weeks in the presence of NAD or cNAD at 32° C. and 83% relative air humidity.

If a mutant is used instead of the wild-type enzyme (from *Bacillus subtilis*), it is possible to further increase the residual activity of GlucDH. After 24 weeks storage at 32° C. and 85% relative air humidity in the presence of cNAD, the residual activity of a mutant GlucDH_E96G_E170K with the amino acid substitutions glutamic acid→glycine at position 96 and glutamic acid→lysine at position 170 (GlucDH-mut1) of the wild-type enzyme is about 70%, whereas the residual activity of a mutant GlucDH_E170K_K252L with the amino acid substitutions glutamic acid→lysine at position 170 and lysine→leucine at position 252 (GlucDH-mut2) is about 50% (FIG. 8).

Figure 9A:
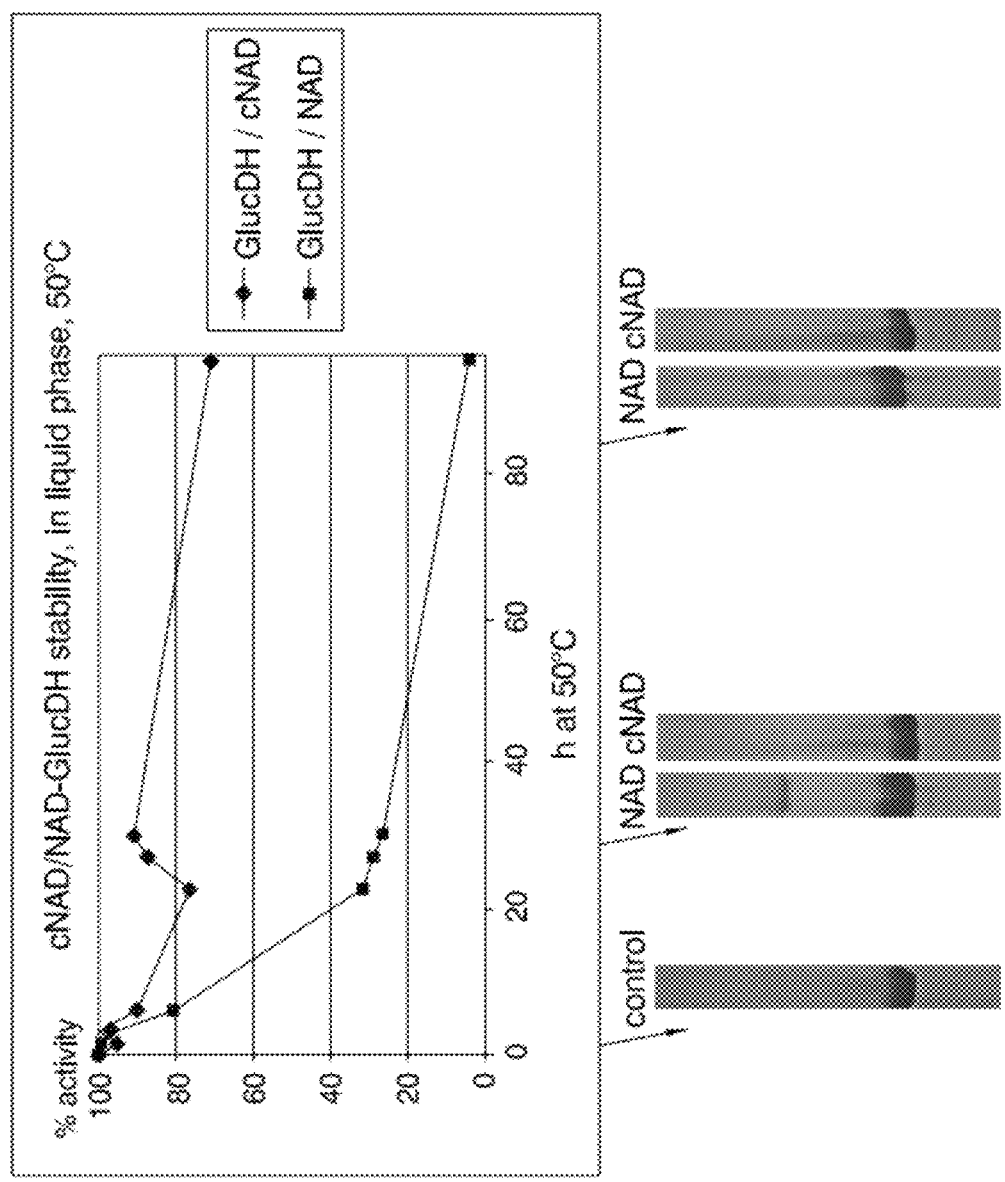
FIGS. 9A and 9B are graphical illustrations of the stability of glucose dehydrogenase in the presence of NAD or cNAD in a liquid phase at 50° C. for a period of 4 days (FIG. 9A) or 14 days (FIG. 9B) with test conditions of 10 mg/ml GlucDH; 12 mg/ml NAD or cNAD; buffer: 0.1 M Tris, 1.2 M NaCl, pH 8.5; temperature 50° C.
Figure 9B:
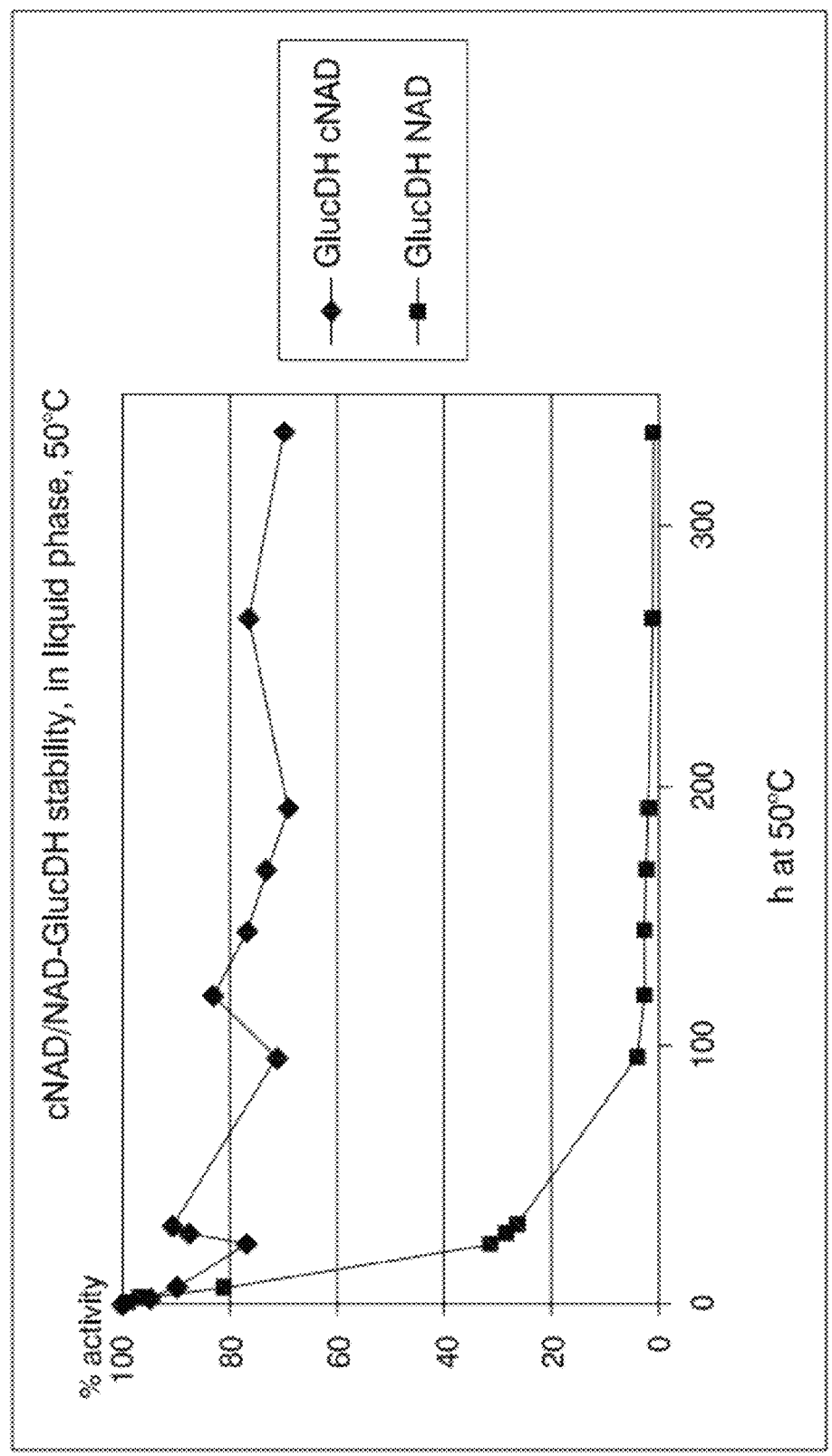

Storage of glucose dehydrogenase in a liquid phase also clearly shows the difference between NAD and cNAD (FIGS. 9A and 9B). After 95 hours at 50° C. the residual activity of glucose dehydrogenase in the presence of the native coenzyme NAD is >>5%, whereas the residual activity of GlucDH in the presence of the artificial coenzyme cNAD is 75% (FIG. 9A). After 336 hours storage at 50° C. the residual activity of the enzyme stabilized with NAD is now only about 1%; a residual activity of still about 70% is observed for the enzyme stored in the presence of cNAD. The corresponding SDS gels also show a change in the GlucDH bands in the presence of the native coenzyme NAD: new bands are seen at higher molar masses and there is a shift in the 30 kDa band.

Overall it is an extremely surprising result that the stabilization of the cofactor simultaneously brings about a stabilization of the enzyme—and not just through the cooperative effect of the better cohesion of the enzyme. Decomposition of the cofactor NAD has an adverse effect on the stability of the enzyme GlucDH and even accelerates its inactivation. Replacement of native NAD by artificial analogues allows GlucDH to be stored under stress conditions (e.g. elevated temperatures) even in the presence of a cofactor.

It is possible with such a system to produce blood glucose test strips with considerably improved stability properties for which a presentation without desiccant is possible.

Example 2 cNAD or NAD was added to a detection solution containing alcohol dehydrogenase. These mixtures were stored at 2-8° C. and at 35° C. Subsequently, the stability of alcohol dehydrogenase (ADH) was checked at regular intervals and the residual activity of the enzyme was determined.

Figure 10:
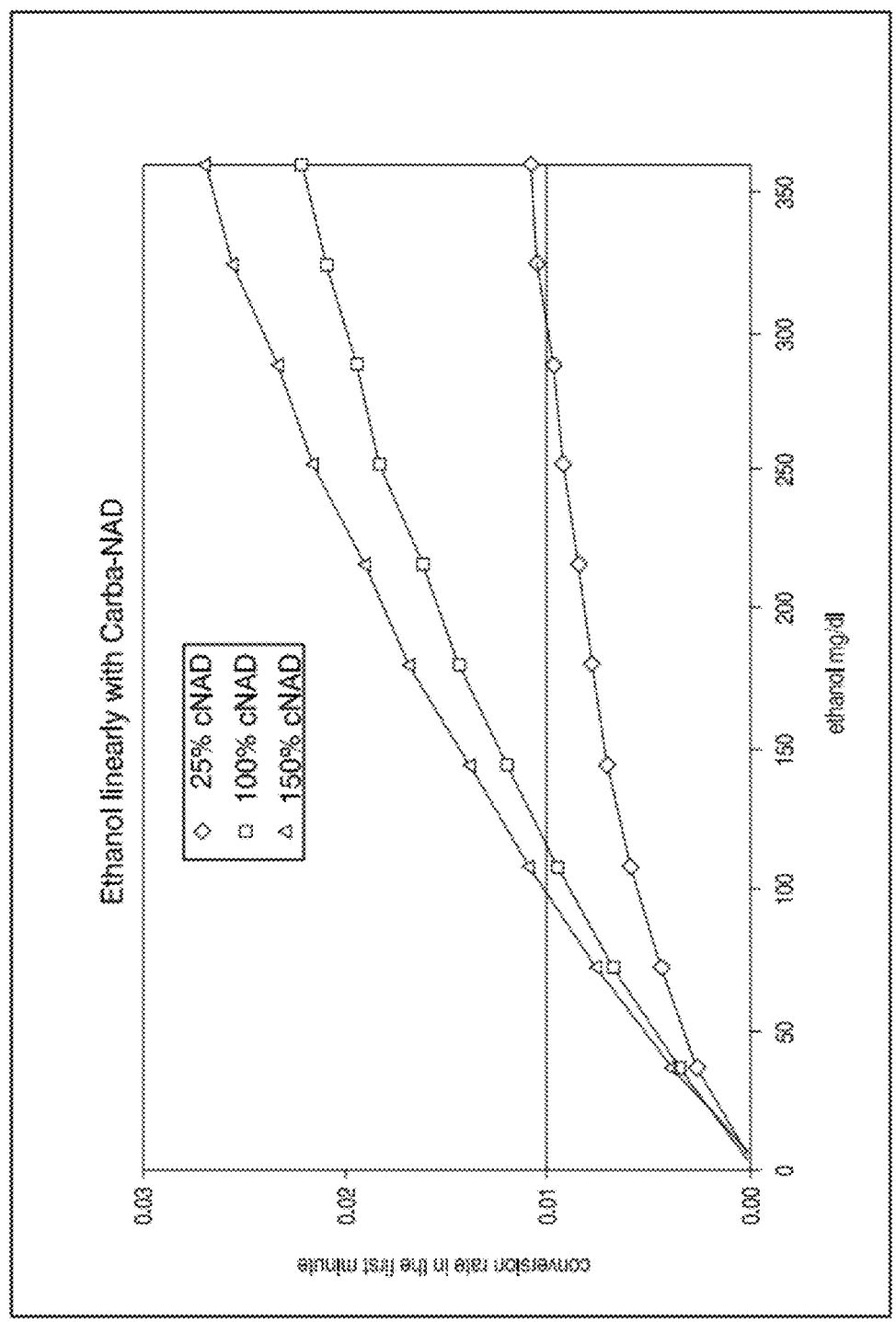
FIG. 10 is a graphical illustration of various function curves of alcohol dehydrogenase in the presence of cNAD where the concentration of cNAD is varied between 25% and 150% based on the initial concentration of NAD in the liquid test.
Figure 11:
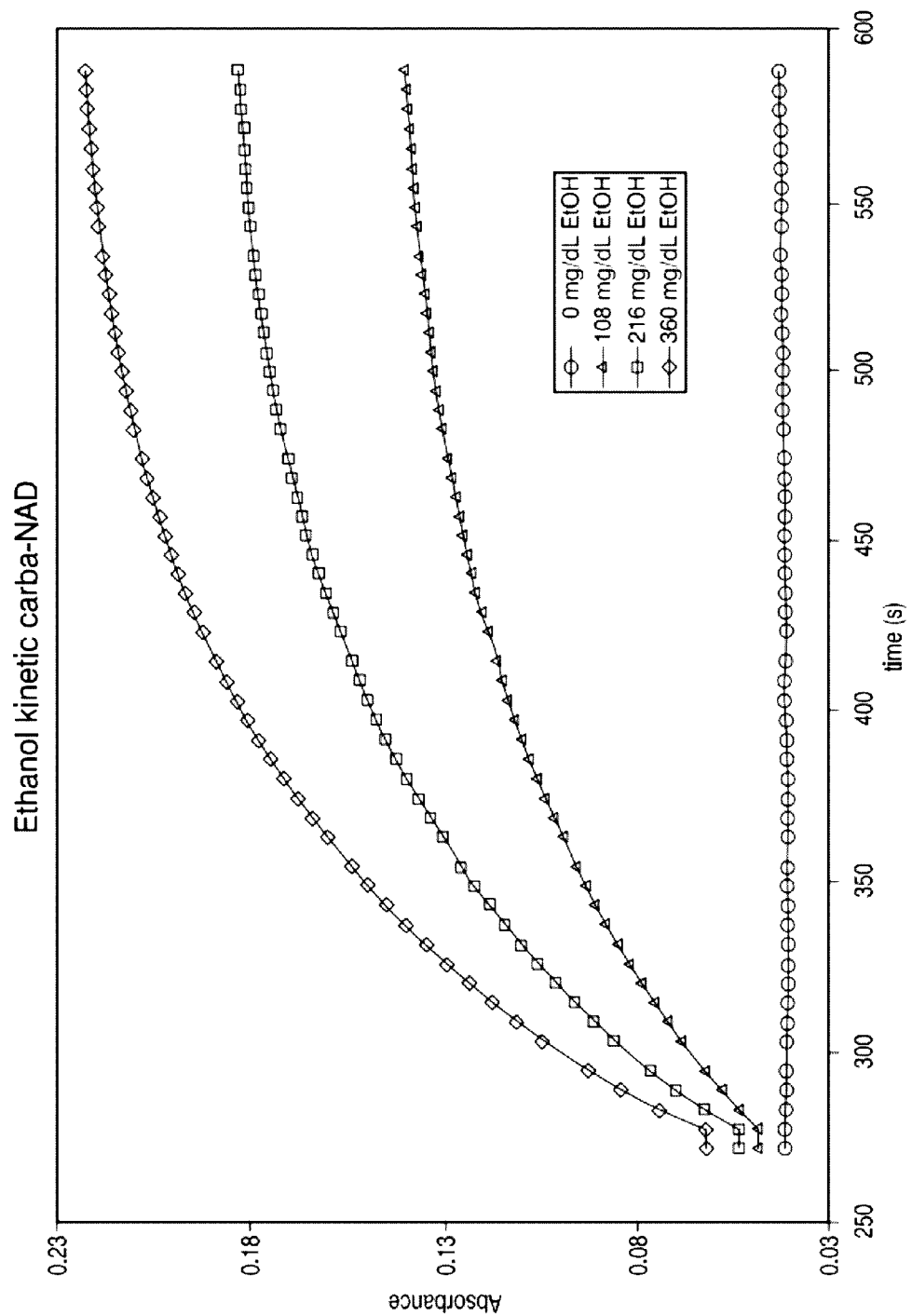
FIG. 11 is a graphical illustration of the results of the enzyme kinetics of alcohol dehydrogenase in the presence of cNAD at various ethanol concentrations.

FIG. 10 shows the linearity of the conversion of ethanol by means of alcohol dehydrogenase (ADH) in the presence of various concentrations of cNAD which demonstrates the practical usability of the enzyme system ADH/cNAD to determine ethanol. Moreover, the kinetics curves of the conversion of ethanol by means of a combination of alcohol dehydrogenase and cNAD show that there is a considerable dependency on the concentration of the substrate where the rate of conversion increases with increasing ethanol concentrations (FIG. 11).

Figure 12:
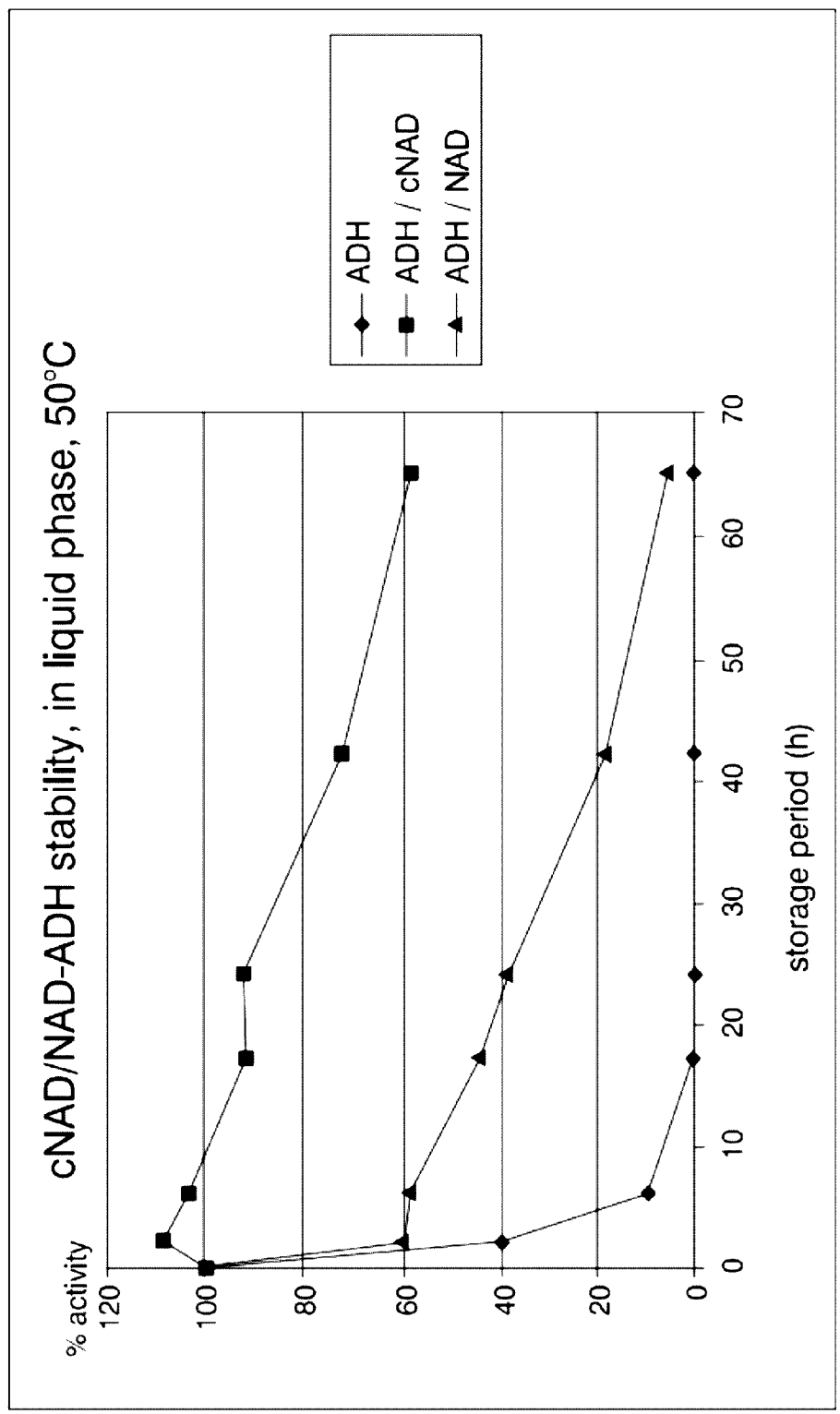
FIG. 12 is a graphical illustration of the stability of alcohol dehydrogenase from yeast in the presence of NAD or cNAD in a liquid phase at 35° C. for a period of 65 hours with test conditions of 5 mg/ml ADH; 50 mg/ml NAD or cNAD; buffer: 75 mM $Na_4P_2O_7$; glycine, pH 9.0; temperature 35° C.

Again, storage in a liquid phase shows the difference between storage in the presence of NAD or cNAD (FIG. 12). The residual activity of alcohol dehydrogenase in the presence of the native coenzyme NAD is at about 6% after 65 hours at 35° C., whereas the residual activity of the enzyme in the presence of the artificial coenzyme cNAD is still at about 60%.

If alcohol dehydrogenase is stored together with native NAD or with cNAD for several months at 2-8° C. in a refrigerator, then one observes in the case of cNAD a considerable decrease in enzyme activity over the entire storage period. Whereas the difference after 2 weeks storage is still slight, there is an approximately 20% higher residual activity of alcohol dehydrogenase after 12 months storage in the presence of 16 mM cNAD compared to a corresponding solution containing 16 mM NAD as the coenzyme. The results are shown in table 1.

TABLE 1

| Ingredient | concentr. (mmol/l) | U/ml (initial value) | % of weighed amount (initial value) | 2 weeks at 2-8° C. (% of initial value) | 3 months at 2-8° C. (% of initial value) | 7.5 months at 2-8° C. (% of initial value) | 10 months at 2-8° C. (% of initial value) | 12 months at 2-8° C. (% of initial value) |
| --- | --- | --- | --- | --- | --- | --- | --- | --- |
| comparable mixture | 16 (NAD) | 142.2 | 85.2 | 96.9 | 92.1 | 80.2 | 70.3 | 60.5 |
| exchange NAD/cNAD | 16 | 120.2 | 71.9 | 100.7 | 91.3 | 95.6 | 88.2 | 83.8 |

The extent of the stabilization in relation to the amount of cNAD used is shown in Table 2. Accordingly, the residual activity of alcohol dehydrogenase can be increased somewhat in samples that have been stored for 2 weeks at 2-8° C. by increasing the concentration of cNAD. In the stress model, which envisages a storage of the enzyme for 2 weeks at 35° C., the decrease of the enzyme activity of alcohol dehydrogenase can, however, be significantly increased by increasing concentrations of cNAD, and in the case of a concentration of 15 mM to cNAD an approximately 45% higher residual activity is observed compared to a solution of the enzyme in the presence of 0.5 mM cNAD.

TABLE 2

| Sample | pH/additive | U/ml (initial value) | % of weighed amount (initial value) | 2 weeks at 2-8° C. (% of initial value) | 2 weeks at 35° C. (% of initial value) |
| --- | --- | --- | --- | --- | --- |
| 1 | pH 7.85 0.5 mM cNAD | 123.1 | 73.7 | 93.8 | 31.1 |
| 2 | pH 7.85 1 mM cNAD | 125.8 | 75.3 | 97.7 | 45.5 |
| 3 | pH 7.85 5 mM cNAD | 125.1 | 74.9 | 101.1 | 74.1 |
| 4 | pH 7.85 15 mM cNAD | 123.7 | 74.1 | 104.0 | 77.6 |

Example 3

Various test systems which each contained glucose dehydrogenase, NAD, a mediator and, where appropriate, an optical indicator, were measured photometrically and electrochemically in order to determine glucose.

For photometric measurements four test elements which had each been stored for 11 weeks at room temperature and contained 2,18-phosphomolybdic acid in addition to glucose dehydrogenase, NAD and a mediator, were initially investigated at various glucose concentrations.

Figure 13:
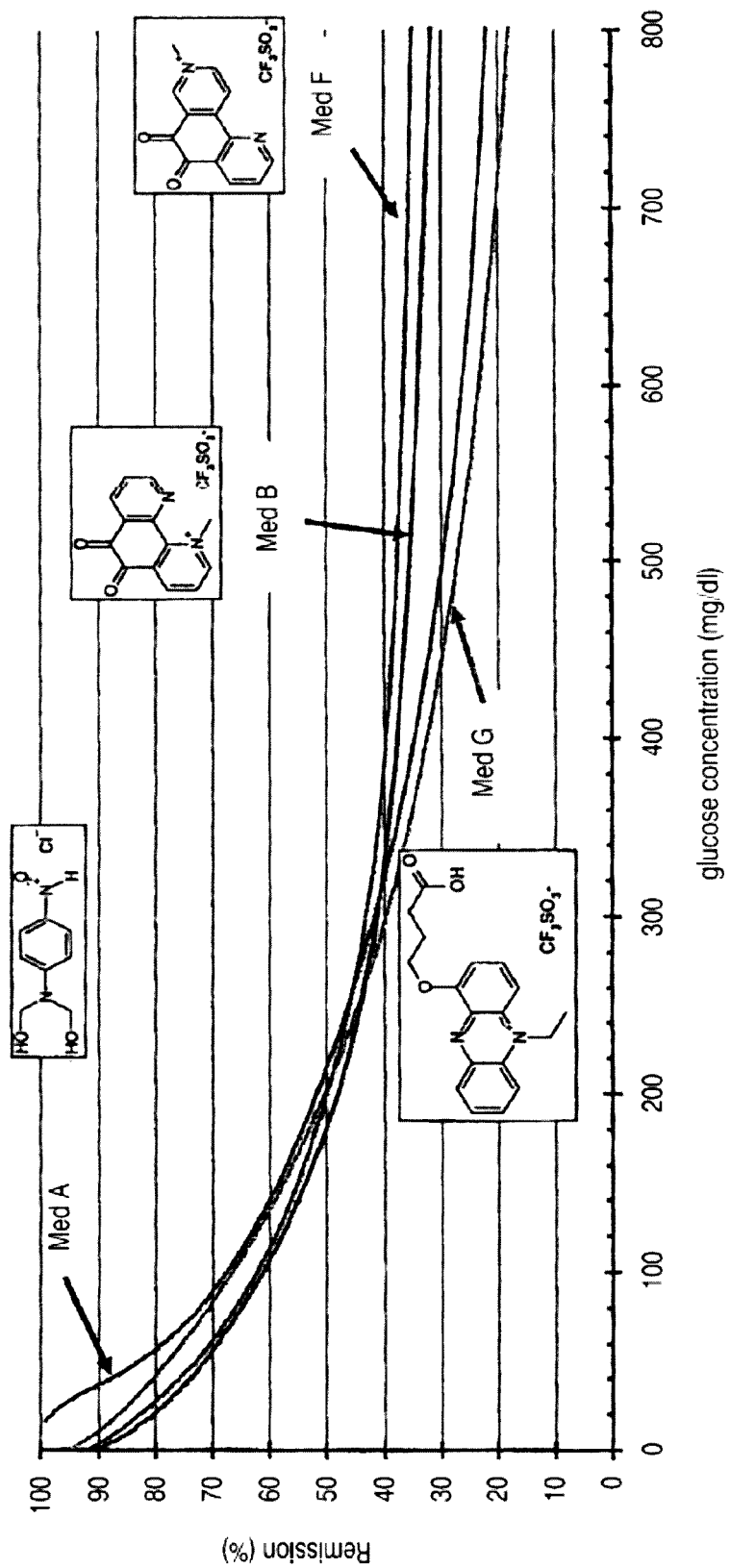
FIG. 13 is a graphical illustration of various function curves of glucose dehydrogenase after 11 weeks storage in the presence of NAD and different mediators at room temperature.

As shown in FIG. 13, a decrease in the reflectance was observed with increasing glucose concentrations for all four mediators that were used; i.e. [(4-nitroso-phenyl)imino] dimethanol hydrochloride (med A), 1-methyl-5,6-dioxo-5, 6-dihydro-1,10-phenanthrolinium-trifluoromethane sulfonate (med B), 7-methyl-5,6-dioxo-5,6-dihydro-1,7-phenanthrolinium-trifluoromethane sulfonate (med F) and 1-(3-carboxy-propoxy)-5-ethylphenazinium-trifluoromethane sulfonate (med G), and thus the above-mentioned mediators are in principle suitable for determining glucose by means of photometry.

Figure 14:
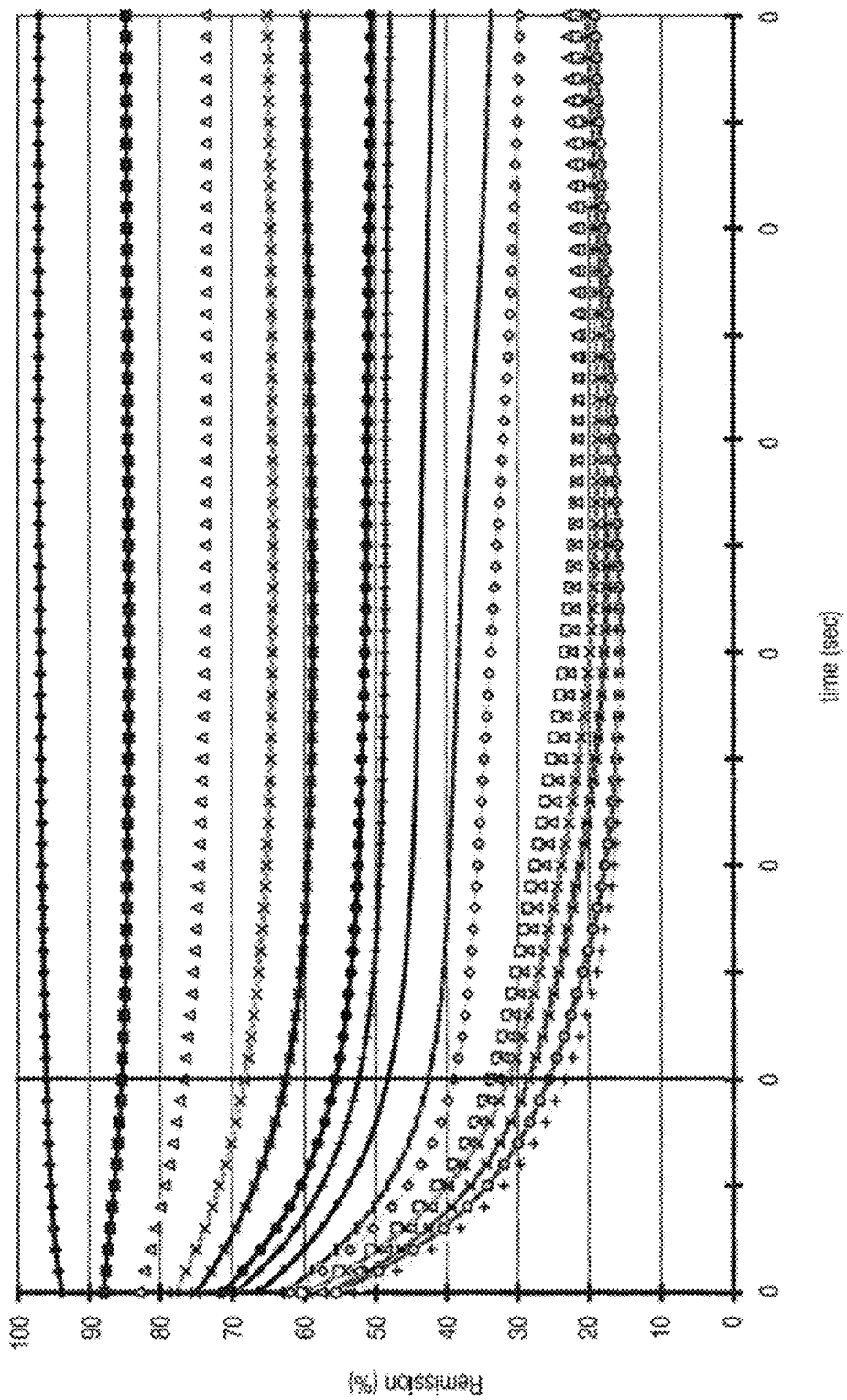
FIG. 14 is a graphical illustration of the results of the enzyme kinetics of glucose dehydrogenase in the presence of NAD and 1-(3-carboxypropoxy)-5-ethylphenazinium-trifluoromethane sulfonate at various glucose concentrations.

At high glucose concentrations in the region of 800 mg/dl the reflectance of the measured sample is still about 20% when using [(4-nitrosophenyl)imino]di-methanol hydrochloride or 1-(3-carboxypropoxy)-5-ethylphenazinium-trifluoromethane sulfonate suggesting that these two mediators are particularly suitable for photometric measurements using the glucose dehydrogenase/NAD system, and thus also the glucose dehydrogenase/cNAD system. The kinetics of the conversion of glucose using the system glucose dehydrogenase, NAD, 1-(3-carboxypropoxy)-5-ethylphenazinium-trifluoromethane sulfonate and 2,18-phosphomolybdic acid at glucose concentrations in the range from 0 to 800 mg/dl is shown in FIG. 14.

Figure 15:
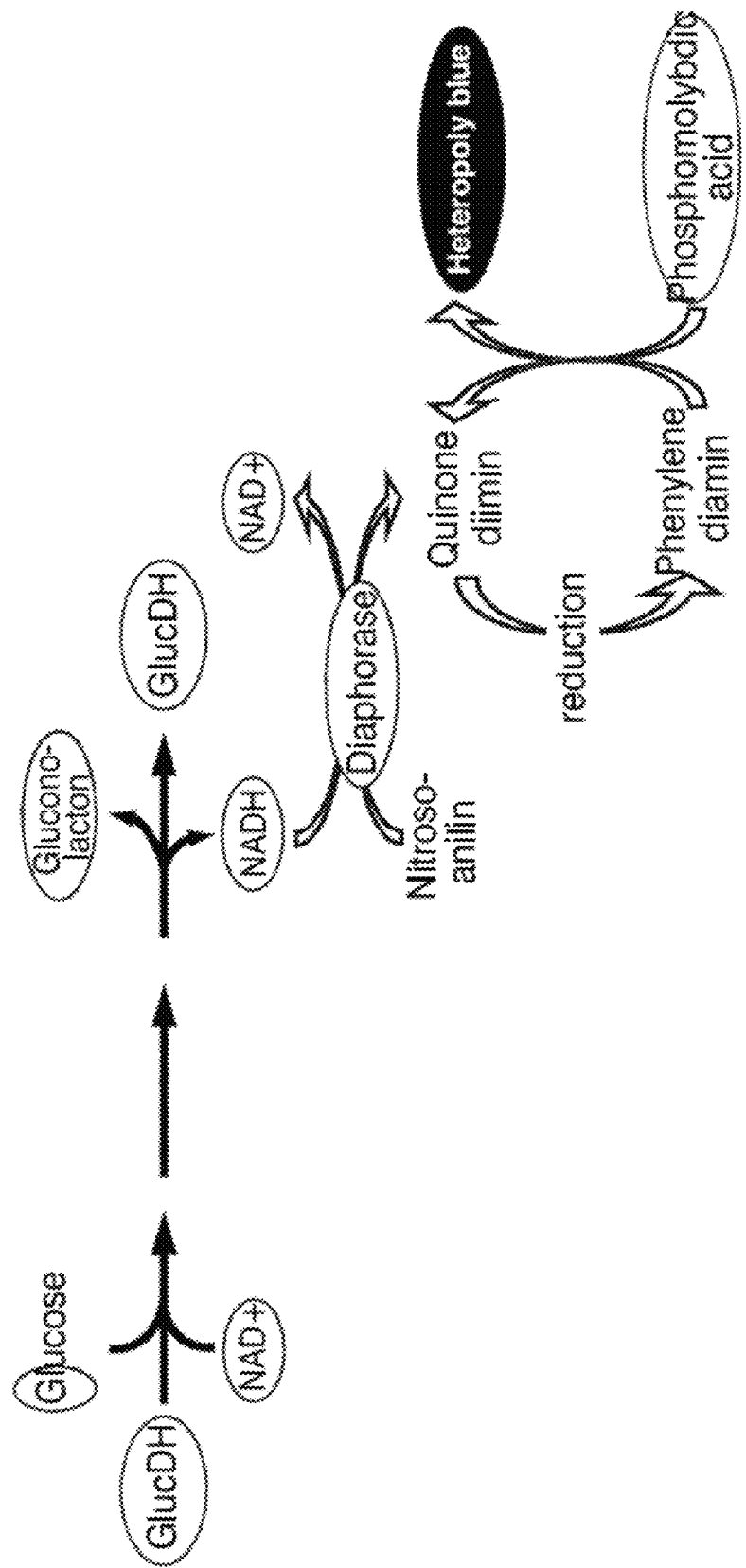
FIG. 15 is a schematic representation of glucose detection using GlucDH as the enzyme and diaphorase as the mediator.
Figure 16:
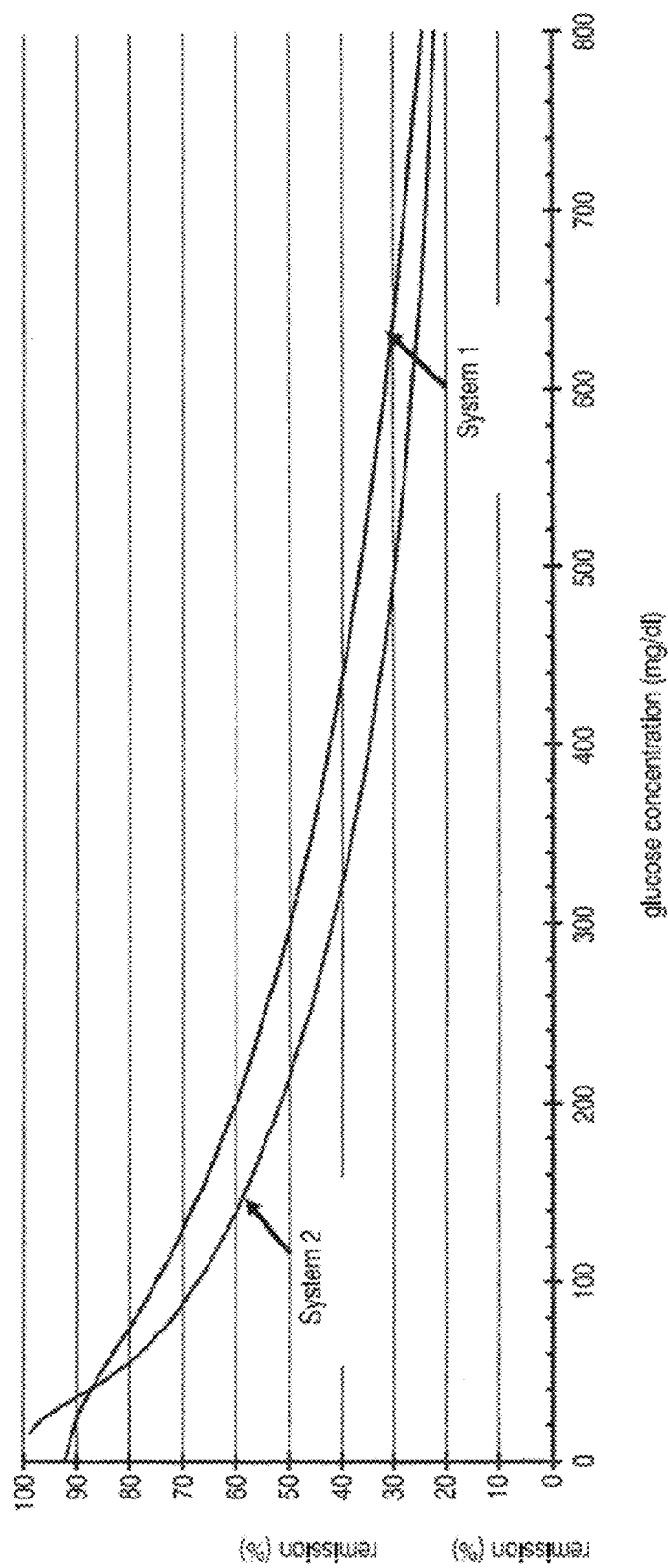
FIG. 16 is a graphical illustration of the function curves of glucose-dye-oxidoreductase (GlucDOR) in the presence of pyrroloquinoline quinone (PQQ) and [(4-nitrosophenyl)imino]dimethanol hydrochloride as the mediator and of glucose dehydrogenase in the presence of NAD and diaphorase/[(4-nitrosophenyl)imino]-dimethanol hydrochloride as the mediator.
Figure 17:
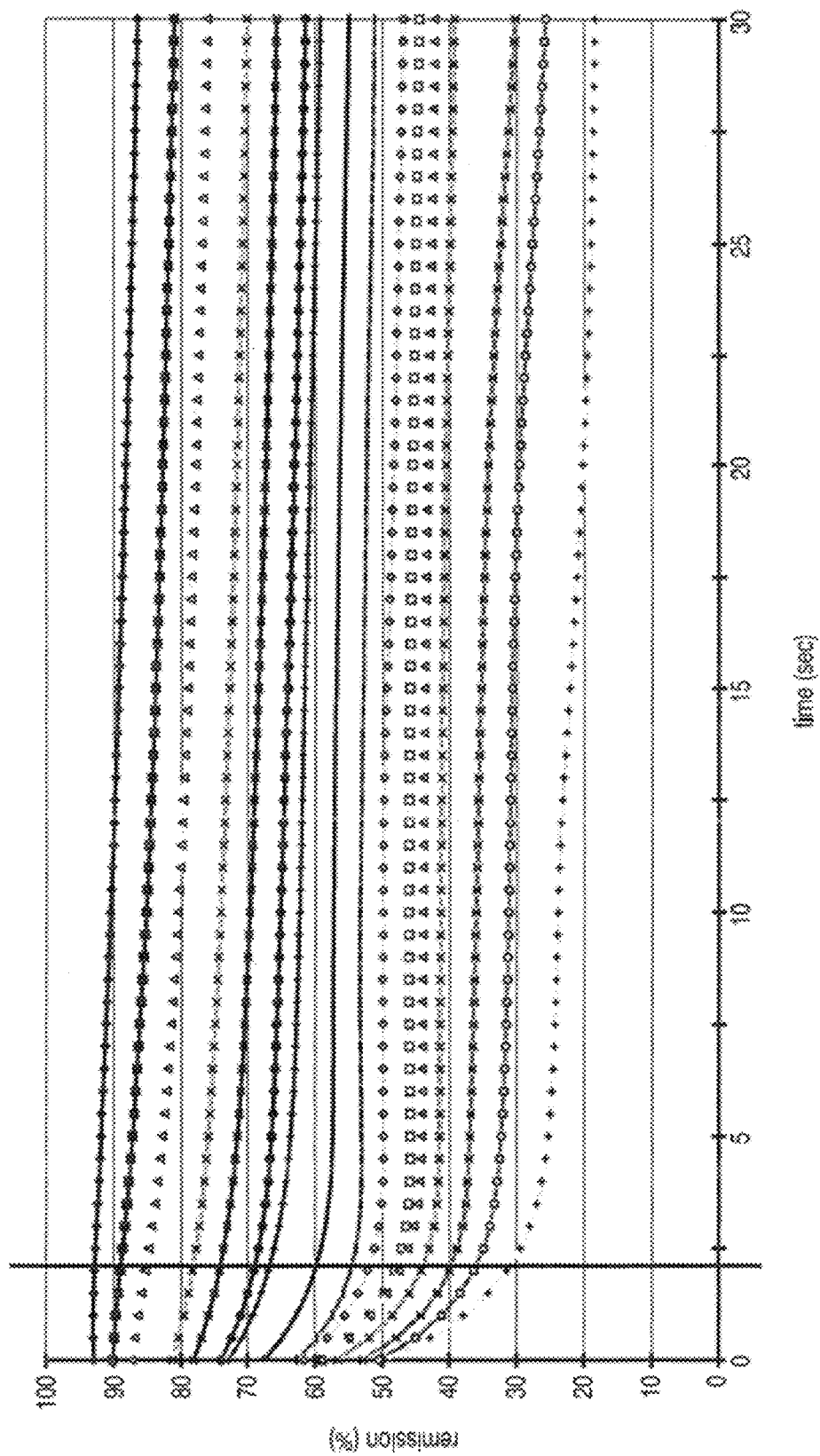
FIG. 17 is a graphical illustration of the results of the enzyme kinetics of glucose dehydrogenase in the presence of NAD and diaphorase at various glucose concentrations.

The schematic representation in FIG. 15 shows that the photometric determination of glucose can also take place with the (additional) use of diaphorase as an intermediary mediator. FIG. 16 shows a concentration-dependent decrease in reflectance for the glucose dehydrogenase, NAD, diaphorase, [(4-nitrosophenyl)-imino]dimethanol hydrochloride and 2,18-phosphomolybdic acid system (system 1). The glucose-dye-oxidoreductase, pyrroloquinoline quinone, [(4-nitroso-phenyl)imino]dimethanol hydrochloride and 2,18-phosphomolybdic acid system (system 2) served as a comparison which likewise causes a concentration-dependent decrease in the reflectance but has disadvantages because of the low specificity of glucose-dye-oxidoreductase. The kinetics of the conversion of glucose using system 1 is shown in FIG. 17 for glucose concentrations in the range from 0 to 800 mg/dl.

Figure 18:
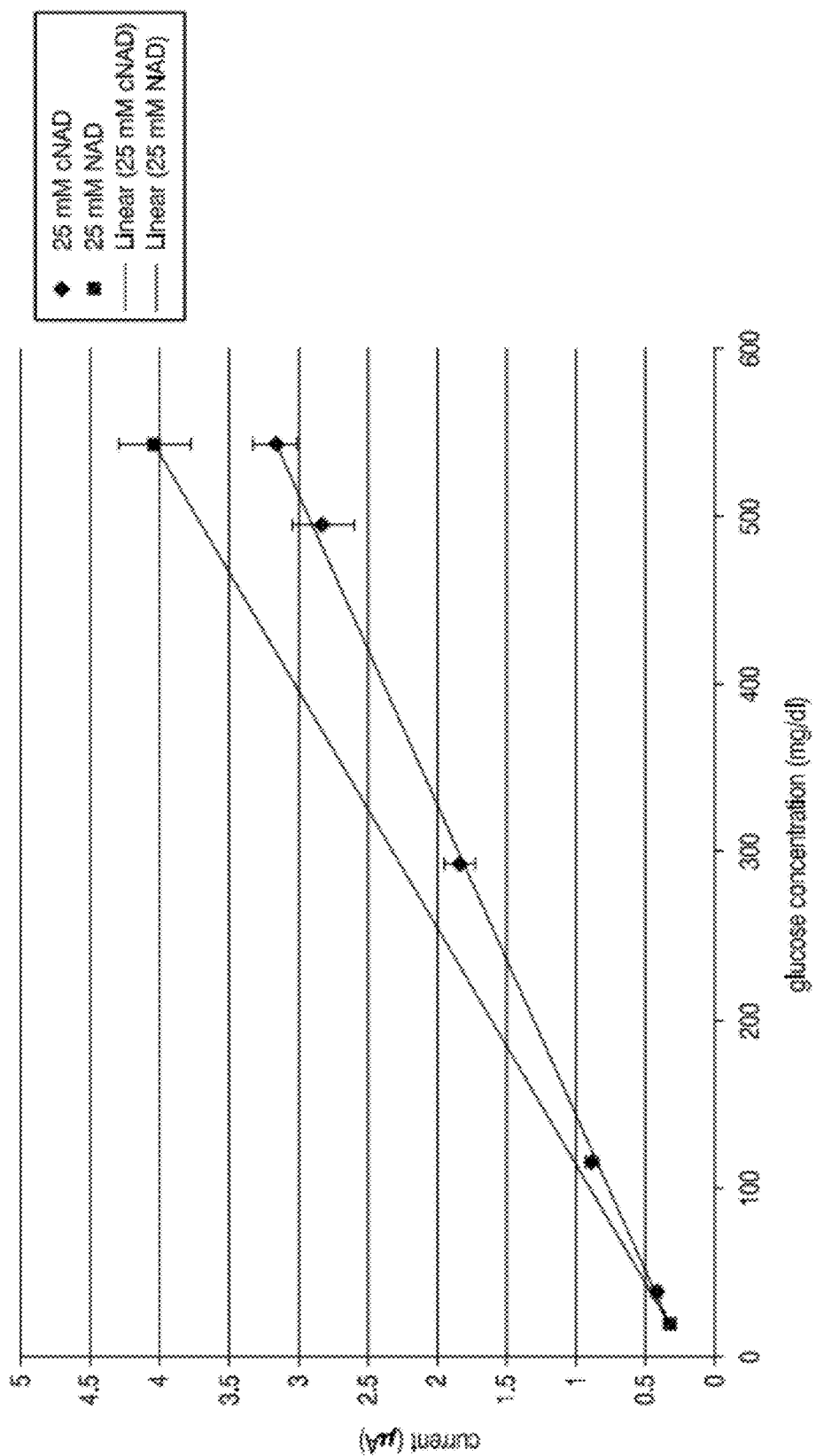
FIG. 18 is a graphical illustration of the current measured as a function of the glucose concentration in the electrochemical determination of glucose using glucose dehydrogenase in the presence of NAD or cNAD with test conditions of 25 mM NAD or cNAD; 2.5 seconds delay; 5 seconds measurement time.

As an alternative to photometry, an electrochemical measurement can also be used for the purposes of determining analytes. Thus, the current required to reoxidize the reduced mediator was found to be linearly dependent on the glucose concentration (FIG. 18) both for a test element which besides glucose dehydrogenase, contained NAD as a coenzyme and 1-(3-carboxypropoxy)-5-ethylphenazinium-trifluoromethane sulfonate as a mediator, and for a corresponding system which contained the stabilized coenzyme cNAD instead of NAD.

It has thus been shown that the analyte determination can be carried out using the dehydrogenase/stabilized coenzyme system as well as by means of electrochemical detection and evaluation at another wavelength which is independent of the coenzyme. The overall formulation should also be further stabilized by the use of the stabilized enzyme/coenzyme pair.

Example 4

In order to determine their stability towards ambient light, various test systems which each contained an enzyme selected from glucose dehydrogenase (GlucDH), glucose-6-phosphate dehydrogenase (G6PDH) and glucose dehydrogenase mutant 2 (GlucDH-mut2) in combination with NAD or carbaNAD were prepared in accordance with the methods described in International Patent Publication No. WO 03/097859 A2 and subsequently a blood sample was added. In particular, the test systems were prepared by applying a photopolymerizable liquid composition including an enzyme and coenzyme to a support and subsequently irradiating the composition with light at a wavelength of 360 nm and 400 W for 10 seconds to obtain reagent layers having a thickness of 12-15 μm. Detection was carried out in the fluorescence mode for a period of several minutes.

Figure 19:
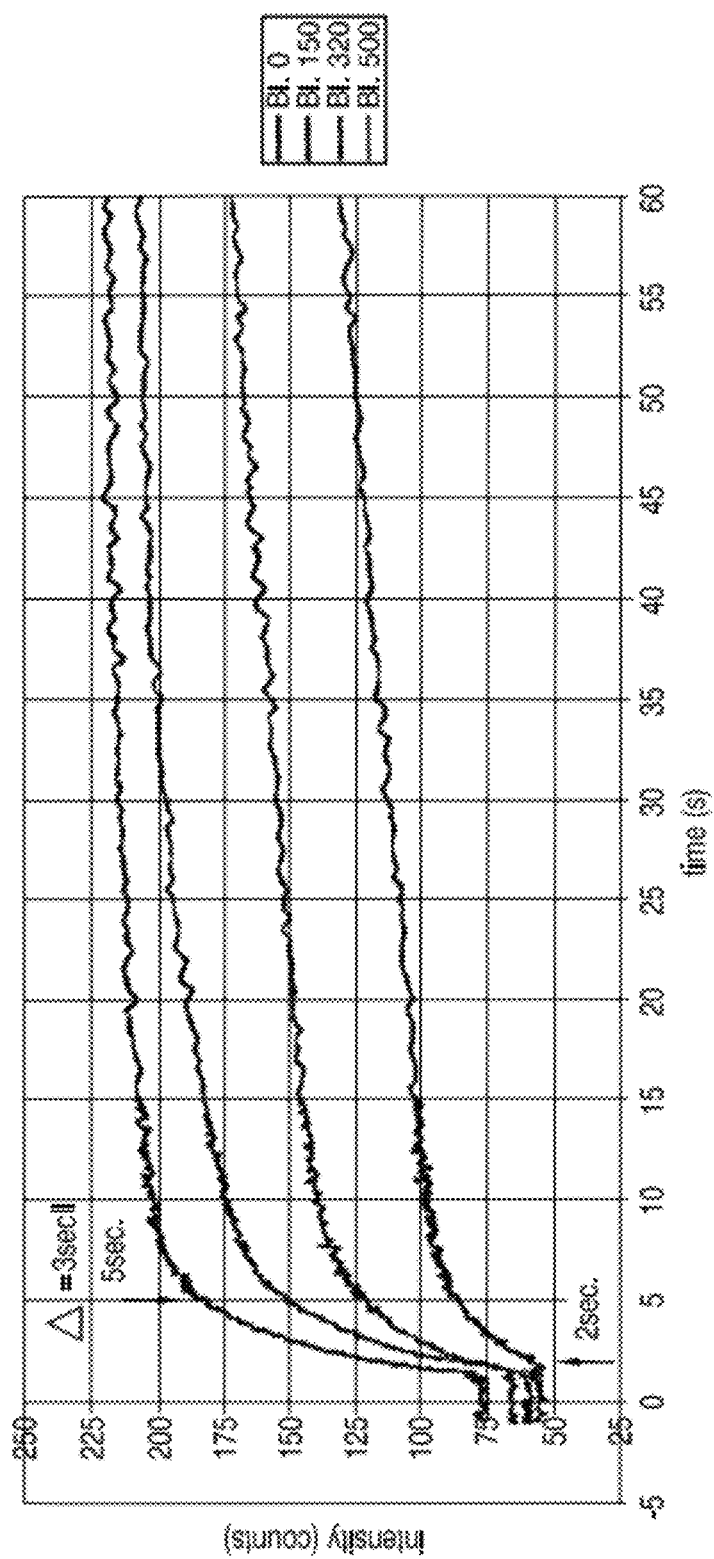
FIG. 19 is a graphical illustration of various function curves of glucose dehydrogenase in the presence of NAD after irradiation by UV light at a wavelength of 360 nm.
Figure 20:
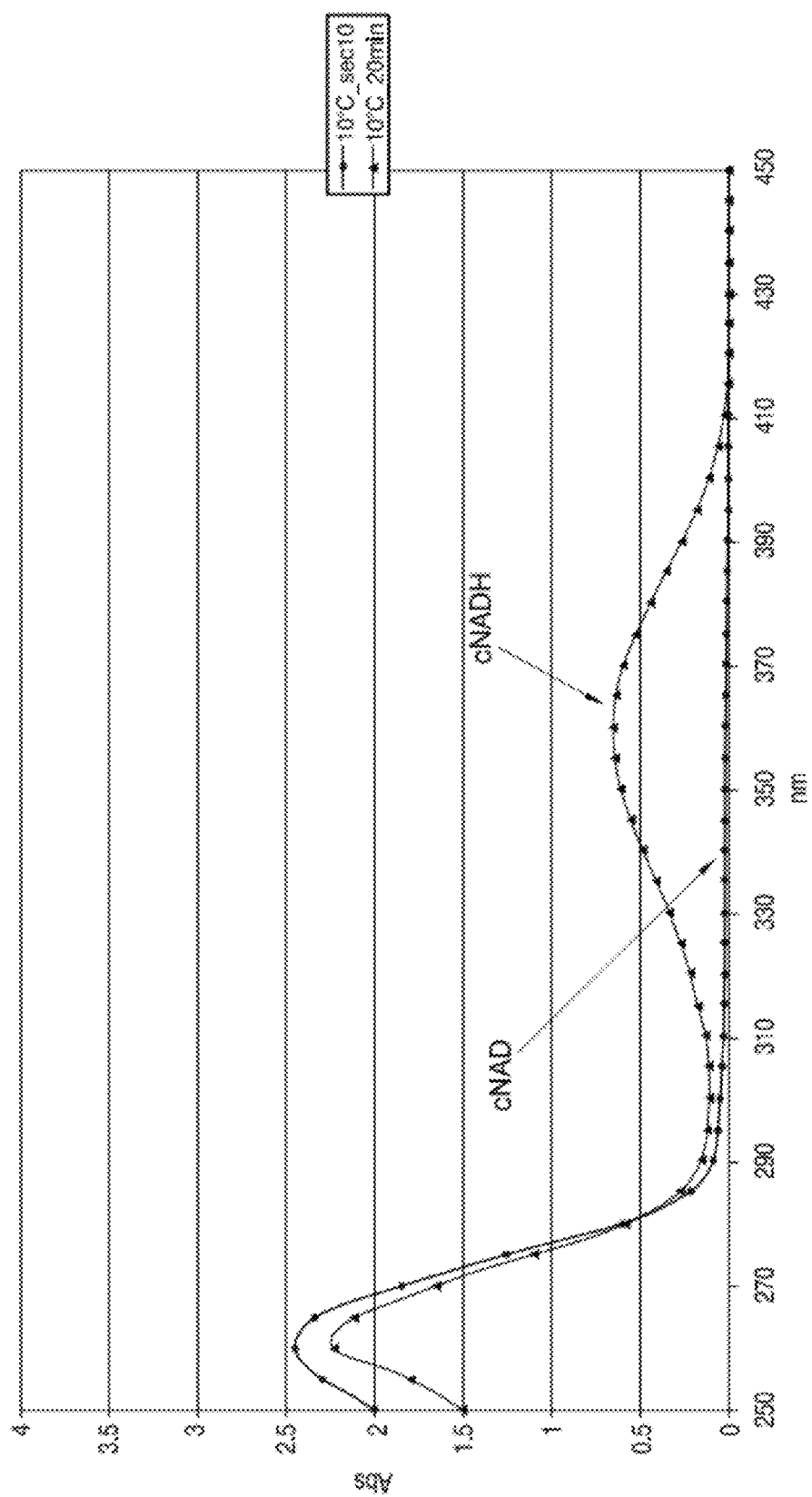
FIG. 20 is a graphical illustration of the absorption spectrum of cNAD and cNADH in the wavelength range of 250-450 nm.

FIG. 19 shows the results of the measurements for the GlucDH/NAD system. As shown by the graph, no reduction of fluorescence whatsoever was observed over the entire measurement period which allows the conclusion that even irradiation of the reagent layer lasting several minutes with energy-rich radiation does not impair the reagent layer due to the lack of absorption of the GlucDH/NAD system in the region ≥300 nm. Taking into consideration the fact that the G6PDH/NAD system and the carbaNAD-containing systems GlucDH/carbaNAD, G6PDH/carbaNAD and GlucDH-mut2/carbaNAD do not absorb in the wavelength region ≥300 nm (FIG. 20), all these systems also have a high stability towards ambient light (results not shown).

Example 5

Specific examples of compositions that can be used to produce the diagnostic test elements described herein are specified in the following.

a) Liquid Reagent for Determining the Activity of Lactate Dehydrogenase

A liquid reagent which, among others, contained diaphorase, carbaNAD, a tetrazolium salt and lactate was used to determine the activity of lactate dehydrogenase. The detection reagent which was stored in solution at 25° C. contained the following ingredients:

3 U/ml diaphorase (from porcine heart)
2 mM carbaNAD or 0.2 mM NAD
2 mM tetrazolium salt WST-3
50 mM Na lactate
0.1 M tricine/HCl, pH 8.8

A measurement of the activity of diaphorase at various storage times showed a considerably increased residual activity of the formulation containing carbaNAD compared to a corresponding formulation containing NAD as the coenzyme.

b) Test Strips for the Determination of Blood Glucose

A composition which, among others, contained glucose dehydrogenase (GlucDH), carbaNAD, diaphorase, nitrosoaniline and phosphomolybdic acid was used to determine blood glucose. Test strips were obtained by applying a first formulation to a polycarbonate foil using a doctor blade (layer height 100 μm), drying the first layer, applying a second formulation to the first layer (doctor blade gap 30 μm), and drying the second layer. The test strips were stored at 32° C. and 30-70% relative air humidity. The formulations used for the first and second layers are shown in Table 3:

TABLE 3

| Ingredients | 1st layer | 2nd layer |
|---|---|---|
| xanthan gum | 0.09 g | — |
| sodium aluminium silicate | 5.00 g | — |
| polyvinyl propionate dispersion (50% by weight in water) | 4.80 g | 5.80 g |
| methyl vinyl ether-maleic acid copolymer | — | 1.40 g |
| titanium dioxide | — | 14.00 g |
| NaOH 16% | — | 2.80 g |
| silicic acid | — | 2.50 g |
| phosphate buffer 0.1M | 13.80 g | 4.40 g |
| N-octanoyl-N-methyl-glucamide | 0.17 g | 0.34 g |
| Na-methyl oleyl taurate | 0.03 g | 0.03 g |
| polyvinyl pyrrolidone (MW 25000) | 0.85 g | 1.80 g |
| tetraethylammonium chloride | 0.12 g | — |
| Bis-(2-hydroxyethyl)-(4-hydroxyiminocyclohexa-2,5-dienylidine)-ammonium chloride | 0.10 g | — |
| 2,18-phosphomolybdic acid, hexasodium salt | 0.50 g | — |
| NaCl | 1.00 g | — |
| carbaNAD (or NAD) | 1.00 g (0.10 g) | — |
| Diaphorase | 1.94 g (203 KU) | — |
| glucose dehydrogenase | 0.97 g (207 KU) | — |
| Hexanol | 0.17 g | 0.16 g |
| 2-methoxy-propanol | 4.30 g | 4.30 g |

The activity of diaphorase was measured at various storage times by extracting the enzyme from the test strip and in the case of the formulation containing carbaNAD a considerably increased residual activity was observed compared to the formulation containing NAD.

c) Test Strips for the Determination of Triglycerides

A composition which, among others, contained glycerol dehydrogenase, carbaNAD, diaphorase and a tetrazolium salt was used to determine triglycerides. Test strips were obtained by applying the formulation mentioned in Table 4 to a polycarbonate foil by means of a doctor blade (layer height 80 μm) and subsequent drying, and they were stored at 32° C. and 30-70% relative air humidity.

TABLE 4

| Ingredients | Amount |
|---|---|
| xanthan gum | 0.30 g |
| silicic acid (Aerosil) | 5.00 g |
| polyvinylproprionate dispersion (50% by weight in water) | 6.00 g |
| titanium dioxide | 18.00 g |
| N-octanoyl-N-methyl-glucamide | 0.20 g |
| polyvinyl pyrrolidone (MW 25000) | 0.40 g |
| Tricine | 0.30 g |
| HCl | ad pH 8.5 |
| lipase (porcine pancreas), 12 KU/g | 5.00 g |
| glycerol dehydrogenase, 100 U/mg | 1.00 g |
| carbaNAD (or NAD) | 1.60 g (0.20 g) |
| diaphorase, 20 U/mg | 2.00 g |
| WST-5 | 2.00 g |
| Water | 82.00 g |

The activity of diaphorase was measured at various storage times by extracting the enzyme from the test strip and in the case of the formulation containing carbaNAD a considerably increased residual activity was observed compared to the formulation containing NAD.

Example 6

In order to evaluate the stabilization of glucose dehydrogenase and diaphorase by carbaNAD, a number of test strips were prepared in analogy to Example 5. The formulations used for the first and the second layer of the test strip are shown in Table 5.

The test strips were stored over a period of 18 weeks at temperatures of 5° C. (KS, refrigerator), 25° C. (RT), 30° C. (GT), 35° C. (DT) and 45° C. (HT), and the enzyme activity in the test strips was determined at the start of storage (0 weeks), after 6 weeks, after 9 weeks, after 12 weeks and after 18 weeks. The results are shown in Table 6 (glucose dehydrogenase) and in Table 7 (diaphorase).

TABLE 6

| Storage temperature | Coenzyme | Enzyme activity (U/cm$^2$) | | | | | Target |
|---|---|---|---|---|---|---|---|
| | | 0 weeks | 6 weeks | 9 weeks | 12 weeks | 18 weeks | |
| KS | NAD | 14.6 | 16.5 | 16.6 | 14.4 | 13.8 | 25.4 |
| RT | | | 15.8 | 14.4 | 12.9 | 12.2 | |
| GT | | | n.d. | n.d. | 9.7 | 9.1 | |
| DT | | | 12.9 | 10.9 | 9.4 | 8.5 | |
| HT | | | 7.8 | 6.2 | n.d. | n.d | |
| KS | carbaNAD | 19.8 | 20.4 | 21.2 | 18.5 | 18.8 | 25.8 |
| RT | | | 20.7 | 21.5 | 18.0 | 17.7 | |
| GT | | | n.d. | n.d. | 17.6 | 16.8 | |
| DT | | | 19.8 | 20.2 | 17.2 | 16.9 | |
| HT | | | 19.0 | 18.8 | n.d | n.d | |

TABLE 7

| Storage temperature | Coenzyme | Enzyme activity (U/cm$^2$) | | | | | Target |
|---|---|---|---|---|---|---|---|
| | | 0 weeks | 6 weeks | 9 weeks | 12 weeks | 18 weeks | |
| KS | NAD | 2.7 | 2.2 | 2.4 | 3.3 | 3.7 | 6.3 |
| RT | | | 2.3 | 2.2 | 2.8 | 3.4 | |
| GT | | | n.d | n.d. | 2.4 | 2.8 | |
| DT | | | 1.5 | 1.8 | 2.4 | 2.8 | |
| HT | | | 1.5 | 1.1 | n.d. | n.d. | |
| KS | carbaNAD | 4.6 | 4.4 | 5.2 | 4.8 | 7.0 | 10.4 |
| RT | | | 4.5 | 5.1 | 4.6 | 6.7 | |
| GT | | | n.d. | n.d. | 4.3 | 6.2 | |
| DT | | | 3.4 | 4.4 | 4.0 | 5.3 | |
| HT | | | 3.9 | 3.8 | n.d. | n.d. | |

TABLE 5

| Ingredients | 1st layer | 1st layer | 2nd layer |
|---|---|---|---|
| xanthan gum | 0.29 g | 0.29 g | — |
| Gantrez S97 | — | — | 1.44 g |
| tetraethylammonium chloride | 0.07 g | 0.07 g | 0.45 g |
| Mega 8 | 0.17 g | 0.17 g | 0.36 g |
| Geropon T77 | 0.03 g | 0.03 g | 0.03 g |
| polyvinyl pyrrolidone (MW 25000) | 0.87 g | 0.87 g | 1.99 g |
| Transpafill (or silicic acid) | 4.82 g (4.79 g) | 4.82 g (4.79 g) | — |
| silicic acid | — | — | 16.02 g |
| titanium dioxide | — | — | 2.18 g |
| Propiofan | 5.04 g | 5.02 g | 6.14 g |
| N,N-bis-(2-hydroxyethyl)-4-nitrosoaniline | 0.10 g | 0.10 g | 0.16 g |
| 2,18-phosphomolybdic acid, hexasodium salt | 0.33 g | 0.33 g | 1.98 g |
| K/Na buffer 0.1M | 10.00 g | 9.96 g | — |
| NAD | 0.58 g | — | — |
| carbaNAD | — | 4.00 g | — |
| glucose dehydrogenase, mutant 2 | 1.06 g (324 KU) | 1.06 g (324 KU) | — |
| Diaphorase | 0.78 g (80 KU) | 1.26 g (130 KU) | — |
| K$_3$[Fe(CN)$_6$] | 0.01 g | 0.01 g | 0.01 g |
| NaOH 16% | 0.25 g | 0.28 g | 2.69 g |
| tert. amyl alcohol | 1.00 g | 1.00 g | 1.07 g |

As shown in Tables 7 and 8, storage of glucose dehydrogenase and diaphorase in the presence of carbaNAD over a period of 18 weeks allows a high enzyme activity to be maintained while the degradation rate of the enzymes in the presence of NAD is considerably more pronounced.

Example 7

In order to determine the influence of NAD and carbaNAD on the thermostability of various dehydrogenases, the enzymes (1 mg/ml) were dialysed in a first step against the respective measurement buffer for 20 hours at 4° C. Subsequently, 3.8 mM NAD or carbaNAD was added to the samples and the samples were kept at 4° C.

In order to determine the binding of NAD or carbaNAD to the various dehydrogenases, a dynamic differential scanning calorimetry (DSC) was carried out in which the calorimetric scans were carried out at temperatures between 20° C. and 100° C. and at a scan rate of 120° C./h and each sample was measured in triplicate.

The DSC device was cleaned and calibrated according to the MicroCal handbook before carrying out the measurements in order to ensure a correct operation. Lysozyme (1 mg/ml) in 0.1 M glycine-HCl pH 2.4 was measured in duplicate as a control before and after each scan process. Measuring cells, valve and syringe were washed three times with water after every six injections. The data was analysed using the MicroClas Origin software. Glucose dehydrogenase mutant2 in Tris buffer, pH 8.0 led to well-defined peaks in the absence as well as in the presence of NAD and the melting point ($T_M$) was 79.1° C. in the absence of NAD and 80.8° C. in the presence of NAD. Thus, the binding of the glucose dehydrogenase mutant2 to NAD resulted in a $T_M$ shift of more than 1.5° C. With the exception of alcohol dehydrogenase, $T_M$ was also increased in the case of other dehydrogenases, for example in the case of wild-type glucose dehydrogenase, when the enzyme was contacted with NAD or carbaNAD.

Table 8 shows the data obtained by DSC analysis for the various dehydrogenases where in each case experimental conditions were selected which resulted in a single peak in the DSC spectrum. The effect of binding NAD or carbaNAD to the dehydrogenase was compared in each case with scans in which no coenzyme (ligand) was present. In each case 0.1 M Tris buffer, pH 8.5 was used as the measurement buffer if not stated otherwise.

TABLE 8

| dehydrogenase | ligand | $\Delta H_{cal}$ (kcal/mol) | $T_M$ (° C.) |
|---|---|---|---|
| alcohol dehydrogenase * | — | 260 | 55.5 |
|  | NAD | 300 | 55.5 |
|  | carbaNAD | 310 | 55.4 |

TABLE 8-continued

| dehydrogenase | ligand | $\Delta H_{cal}$ (kcal/mol) | $T_M$ (° C.) |
|---|---|---|---|
| glucose dehydrogenase (wild-type) | — | 64 | 52.8 |
|  | NAD | 110 | 63.5 |
|  | carbaNAD | 84 | 58.5 |
| D-lactate dehydrogenase ≠ | — | 18 | 58.4 |
|  | NAD | 19 | 60.4 |
|  | carbaNAD | 19 | 59.1 |
| L-lactate dehydrogenase (porcine) | — | 80 | 59.8 |
|  | NAD | 85 | 61.8 |
|  | carbaNAD | 82 | 61.5 |
| L lactate dehydrogenase (from rabbit) | — | 64 | 58.2 |
|  | NAD | 72 | 60.1 |
|  | carbaNAD | 66 | 60.2 |
| malate dehydrogenase ‡ | — | 310 | 42.4 |
|  | NAD | 380 | 45.1 |
|  | carbaNAD | 340 | 43.2 |

\* 0.75M glycine sodium pyrophosphate, pH 9.0
≠ 0.1M Tris buffer, pH 7.5
‡ 0.5M carbonate buffer, pH 10.0

Although embodiments of the invention have been described using specific terms, such description is for illustrative purposes only, and it is to be understood that changes and variations obvious to the skilled artisan are to be considered within the scope of the claims that follow and their equivalents.

What is claimed is:

1. A method for stabilizing an enzyme, which comprises: storing the enzyme in a presence of a stabilized coenzyme, or a salt form thereof, or a reduced form thereof for a period of storage of at least 2 weeks at a temperature of at least 20° C., wherein the enzyme is selected from the group consisting of an alcohol dehydrogenase (EC 1.1.1.2), a glucose-6-phosphate dehydrogenase (EC 1.1.1.49) and a diaphorase (EC 1.6.99.2), wherein the stabilized coenzyme is a compound of general formula (II):

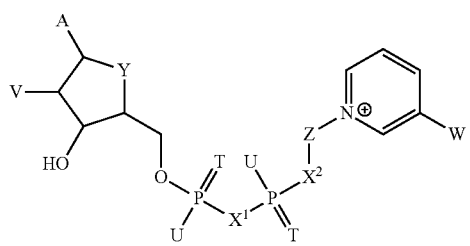

(II)

in which
A=adenine or an analogue thereof;
T=in each case independently denotes O or S;
U=in each case independently denotes OH, SH, $BH_3^-$, or $BCNH_2^-$;
V=in each case independently denotes OH or a phosphate group, or two groups which form a cyclic phosphate group;
W=COOR, $CON(R)_2$, COR, or $CSN(R)_2$ in which R in each case independently denotes H or a $C_1$-$C_2$ alkyl;
$X^1$, $X^2$=in each case independently denote O, $CH_2$, $CHCH_3$, $C(CH_3)_2$, NH, or $NCH_3$;
Y=NH, S, O, or $CH_2$;
Z=a linear residue with 4-6 C atoms or a saturated or an unsaturated carbocyclic or heterocyclic 5-membered ring of general formula (III):

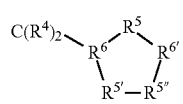

(III)

in which a single or double bond may be present between $R^{5'}$ and $R^{5'''}$, where
$R^4$=in each case independently denotes H, F, Cl, or $CH_3$;
$R^5=CR^4_2$;
$R^{5'}$=O, S, NH, $NC_1$-$C_2$-alkyl, $CR^4$, CHOH, or $CHOCH_3$, and $R^{5''}=CR^4_2$, CHOH, or $CHOCH_3$ if there is a single bond between $R^{5'}$ and $R^{5''}$;
$R^{5'}=R^{5''}=CR^4$ if there is a double bond between $R^{5'}$ and $R^{5''}$; and
$R^6$, $R^{6'}$=in each case independently denote CH or $CCH_3$;
wherein the Z and the pyridine residue are not linked by a glycosidic bond, and
wherein enzyme activity decreases by less than 50% after the period of storage of at least 2 weeks at a temperature of at least 20° C. when compared to an initial value of enzyme activity.

2. The method of claim 1, wherein the stabilized coenzyme comprises carbaNAD.

3. The method of claim 1, wherein the period is at least four weeks.

4. The method of claim 1, wherein the period is at least eight weeks.

5. The method of claim 1, wherein the temperature is at least 25° C.

6. The method of claim 1, wherein the temperature is at least 30° C.

7. The method of claim 1, which includes storing the enzyme in the presence of the stabilized coenzyme with at least one of a relative air humidity of at least 50% and an absence of desiccants.

8. The method of claim 1, which includes storing the enzyme in the presence of the stabilized coenzyme as a dry substance or in a liquid phase.

9. The method of claim 1, which further includes storing the enzyme in the presence of light at a wavelength of 300 nm.

10. The method of claim 1,
wherein enzyme activity decreases by less than 50% after a period of storage of at least 2 weeks at a temperature of at least about 20° C. in a presence of light at a wavelength of ≥300 nm when compared to an initial value of enzyme activity.

11. The method of claim 10, wherein the native coenzyme is one of a native nicotinamide adenine dinucleotide (NAD/NADH) compound and a native nicotinamide adenine dinucleotide phosphate (NADP/NADPH) compound.

* * * * *

SEQUENCE LISTING

```
<160> NUMBER OF SEQ ID NOS: 2

<210> SEQ ID NO 1
<211> LENGTH: 261
<212> TYPE: PRT
<213> ORGANISM: Artificial
<220> FEATURE:
<223> OTHER INFORMATION: Mutant of glucose dehydrogenase from Bacillus
      subtilis
<220> FEATURE:
<221> NAME/KEY: MUTAGEN
<222> LOCATION: (96)..(96)
<220> FEATURE:
<221> NAME/KEY: MUTAGEN
<222> LOCATION: (170)..(170)

<400> SEQUENCE: 1

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Gly
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140
```

Ser Val His Glu Val Ile Pro Trp Pro Leu Phe Val His Tyr Ala Ala
145                 150                 155                 160

Ser Lys Gly Gly Ile Lys Leu Met Thr Lys Thr Leu Ala Leu Glu Tyr
            165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
            195                 200                 205

Val Glu Ser Met Ile Pro Met Gly Tyr Ile Gly Pro Glu Glu Ile
        210                 215                 220

Ala Ala Val Ala Val Trp Leu Ala Ser Lys Glu Ser Ser Tyr Val Thr
225                 230                 235                 240

Gly Ile Thr Leu Phe Ala Asp Gly Gly Met Thr Lys Tyr Pro Ser Phe
                245                 250                 255

Gln Ala Gly Arg Gly
            260

<210> SEQ ID NO 2
<211> LENGTH: 261
<212> TYPE: PRT
<213> ORGANISM: Artificial
<220> FEATURE:
<223> OTHER INFORMATION: Mutant of glucose dehydrogenase from Bacillus
      subtilis
<220> FEATURE:
<221> NAME/KEY: MUTAGEN
<222> LOCATION: (170)..(170)
<220> FEATURE:
<221> NAME/KEY: MUTAGEN
<222> LOCATION: (252)..(252)

<400> SEQUENCE: 2

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Ile Lys Leu Met Thr Lys Thr Leu Ala Leu Glu Tyr
            165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp

-continued

```
                    195                 200                 205
Val Glu Ser Met Ile Pro Met Gly Tyr Ile Gly Glu Pro Glu Glu Ile
    210                 215                 220

Ala Ala Val Ala Val Trp Leu Ala Ser Lys Glu Ser Ser Tyr Val Thr
225                 230                 235                 240

Gly Ile Thr Leu Phe Ala Asp Gly Gly Met Thr Leu Tyr Pro Ser Phe
                245                 250                 255

Gln Ala Gly Arg Gly
                260
```